(12) United States Patent
Panarese et al.

(10) Patent No.: US 11,802,125 B2
(45) Date of Patent: Oct. 31, 2023

(54) FUNCTIONALIZED HETEROCYCLIC COMPOUNDS AS ANTIVIRAL AGENTS

(71) Applicant: Enanta Pharmaceuticals, Inc., Watertown, MA (US)

(72) Inventors: Joseph D. Panarese, Newton, MA (US); Dexter Davis, Watertown, MA (US); Nathaniel Thomas Kenton, Watertown, MA (US); Samuel Bartlett, Brighton, MA (US); Yat Sun Or, Waltham, MA (US)

( * ) Notice: Subject to any disclaimer, the term of this patent is extended or adjusted under 35 U.S.C. 154(b) by 152 days.

(21) Appl. No.: 17/201,308

(22) Filed: Mar. 15, 2021

(65) Prior Publication Data

US 2021/0292320 A1    Sep. 23, 2021

Related U.S. Application Data

(60) Provisional application No. 62/990,118, filed on Mar. 16, 2020.

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01)

(58) Field of Classification Search
CPC .............................. C07D 471/04; A61K 45/06
USPC ........................................................ 514/300
See application file for complete search history.

(56) References Cited

U.S. PATENT DOCUMENTS

| | | | |
|---|---|---|---|
| 3,385,756 A | 5/1968 | Early et al. | |
| 3,975,532 A | 8/1976 | Miller et al. | |
| 4,285,946 A | 8/1981 | Kampe et al. | |
| 4,507,481 A | 3/1985 | Davidson et al. | |
| 5,510,387 A | 4/1996 | Leonidov et al. | |
| 5,656,644 A | 8/1997 | Adams et al. | |
| 6,420,338 B1 | 7/2002 | Schneider et al. | |
| 6,498,165 B1 | 12/2002 | Armstrong et al. | |
| 6,503,913 B1 | 1/2003 | Goldmann et al. | |
| 6,525,069 B1 | 2/2003 | Ko et al. | |
| 6,667,342 B1 | 12/2003 | Clarke et al. | |
| 7,232,825 B2 | 6/2007 | Chen et al. | |
| 7,312,214 B2 | 12/2007 | Qiao et al. | |
| 7,411,003 B1 | 8/2008 | Liu et al. | |
| 7,615,569 B2 | 11/2009 | Fulp et al. | |
| 7,741,494 B2 | 6/2010 | Bressi et al. | |
| 8,101,643 B2 | 1/2012 | Qiu et al. | |
| 8,202,876 B2 | 6/2012 | Albaugh et al. | |
| 8,420,823 B2 | 4/2013 | Sato et al. | |
| 9,447,086 B2 | 9/2016 | Liu et al. | |
| 9,498,479 B2 | 11/2016 | Zhang et al. | |
| 9,573,941 B2 | 2/2017 | Liu et al. | |
| 9,617,252 B2 | 4/2017 | Liu | |
| 9,845,325 B2 | 12/2017 | Fu et al. | |
| 9,938,301 B2 | 4/2018 | He et al. | |
| 10,179,131 B2 | 1/2019 | Qiu et al. | |
| 10,179,792 B2 | 1/2019 | Qiu et al. | |
| 10,189,846 B2 | 1/2019 | Qiu et al. | |
| 10,253,030 B2 | 4/2019 | He et al. | |
| 10,428,070 B2 | 10/2019 | Qiu et al. | |
| 10,538,532 B2 | 1/2020 | Qiu et al. | |
| 10,640,511 B2 | 5/2020 | Qiu et al. | |
| 10,723,733 B2 | 7/2020 | Qiu et al. | |
| 10,729,688 B2 | 8/2020 | Qiu et al. | |
| 10,865,211 B2 | 12/2020 | Panarese et al. | |
| 10,952,978 B2 | 3/2021 | Qiu et al. | |
| 11,058,678 B2 | 7/2021 | Panarese et al. | |
| 2002/0068838 A1 | 6/2002 | Demassey et al. | |
| 2003/0232842 A1 | 12/2003 | Goldmann et al. | |
| 2004/0082619 A1 | 4/2004 | Tada et al. | |
| 2004/0209930 A1 | 10/2004 | Carboni et al. | |
| 2005/0113450 A1 | 5/2005 | Thorarensen et al. | |
| 2005/0203119 A1 | 9/2005 | Ono et al. | |
| 2006/0100233 A1 | 5/2006 | Villa et al. | |
| 2007/0219239 A1 | 9/2007 | Mjalli et al. | |
| 2007/0225373 A1 | 9/2007 | Chen et al. | |

(Continued)

FOREIGN PATENT DOCUMENTS

| | | |
|---|---|---|
| CN | 106928215 A | 7/2017 |
| CN | 106928245 A | 7/2017 |

(Continued)

OTHER PUBLICATIONS

Blaszykowski et al., Journal of Organic Chemistry (2008), 73(5), 1888-1897.*

(Continued)

*Primary Examiner* — Niloofar Rahmani
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, thereof:

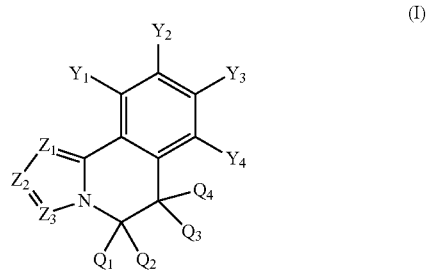

(I)

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

9 Claims, No Drawings

(56) References Cited

U.S. PATENT DOCUMENTS

| | | |
|---|---|---|
| 2009/0023740 A1 | 1/2009 | Fulp et al. |
| 2009/0036420 A1 | 2/2009 | Galley et al. |
| 2009/0118268 A1 | 5/2009 | Riedl et al. |
| 2011/0009622 A1 | 1/2011 | Jitsuoka et al. |
| 2011/0165118 A1 | 7/2011 | Chan et al. |
| 2011/0281950 A1 | 11/2011 | Baiocchi et al. |
| 2012/0009142 A1 | 1/2012 | Karp et al. |
| 2013/0251673 A1 | 9/2013 | Hartman et al. |
| 2013/0267517 A1 | 10/2013 | Guo et al. |
| 2013/0309196 A1 | 11/2013 | Link et al. |
| 2014/0206666 A1 | 7/2014 | Guo et al. |
| 2014/0343032 A1 | 11/2014 | Guo et al. |
| 2014/0357858 A1 | 12/2014 | Ushioda et al. |
| 2015/0005295 A1 | 1/2015 | Hache et al. |
| 2015/0038515 A1 | 2/2015 | Cuconati et al. |
| 2015/0119362 A1 | 4/2015 | Gurney et al. |
| 2015/0133428 A1 | 5/2015 | Velaparthi et al. |
| 2015/0152073 A1 | 6/2015 | Hartman et al. |
| 2015/0152096 A1 | 6/2015 | Zhang et al. |
| 2015/0197493 A1 | 7/2015 | Hartman et al. |
| 2015/0210682 A1 | 7/2015 | Han et al. |
| 2015/0252057 A1 | 9/2015 | Zhu et al. |
| 2015/0266890 A1 | 9/2015 | Vandyck et al. |
| 2015/0274653 A1 | 10/2015 | Vandyck et al. |
| 2016/0115149 A1 | 4/2016 | Vandyck et al. |
| 2016/0185777 A1 | 6/2016 | Hartman et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Ren et al. |
| 2016/0289212 A1 | 10/2016 | Gao et al. |
| 2016/0296515 A1 | 10/2016 | Han et al. |
| 2016/0332996 A1 | 11/2016 | Gao et al. |
| 2016/0347746 A1 | 12/2016 | Zhang |
| 2017/0014408 A1 | 1/2017 | Gao et al. |
| 2017/0022150 A1 | 1/2017 | Gao et al. |
| 2017/0037037 A1 | 2/2017 | Biswas et al. |
| 2017/0197986 A1 | 7/2017 | He et al. |
| 2017/0217974 A1 | 8/2017 | Gao et al. |
| 2017/0240548 A1 | 8/2017 | Fu et al. |
| 2017/0253609 A1 | 9/2017 | Gao et al. |
| 2017/0354641 A1 | 12/2017 | Bastian et al. |
| 2017/0355701 A1 | 12/2017 | Qiu et al. |
| 2017/0355712 A1 | 12/2017 | Campbell et al. |
| 2018/0134723 A1 | 5/2018 | Tets et al. |
| 2018/0312507 A1 | 11/2018 | Fu et al. |
| 2018/0312512 A1 | 11/2018 | He et al. |
| 2019/0060258 A1 | 2/2019 | Qiu et al. |
| 2019/0084994 A1 | 3/2019 | Qiu et al. |
| 2019/0119288 A1 | 4/2019 | Qiu et al. |
| 2019/0144448 A1 | 5/2019 | Kotschy et al. |
| 2019/0144449 A1 | 5/2019 | Kotschy et al. |
| 2019/0177316 A1 | 6/2019 | Qiu et al. |
| 2019/0177320 A1 | 6/2019 | Qiu et al. |
| 2019/0224188 A1 | 7/2019 | Panarese et al. |
| 2019/0298865 A1 | 10/2019 | Cuthbertson et al. |
| 2019/0321360 A1 | 10/2019 | Qiu et al. |
| 2019/0337903 A1 | 11/2019 | Khan |
| 2020/0095258 A1 | 3/2020 | Panarese et al. |
| 2020/0165249 A1 | 5/2020 | Panarese et al. |
| 2021/0079014 A1 | 3/2021 | Panarese et al. |
| 2021/0115060 A1 | 4/2021 | Panarese et al. |

FOREIGN PATENT DOCUMENTS

| | | |
|---|---|---|
| CN | 108530449 A | 9/2018 |
| CN | 108727378 A | 11/2018 |
| CN | 111116577 A | 5/2020 |
| DE | 10109856 A1 | 9/2002 |
| EP | 2280001 A1 | 2/2011 |
| JP | 2010526151 A | 7/2010 |
| JP | 2012526820 A | 11/2012 |
| JP | 2013507350 A | 3/2013 |
| WO | 8702367 A2 | 4/1987 |
| WO | 9504046 A1 | 2/1995 |
| WO | 0168641 A1 | 9/2001 |
| WO | 0168647 A1 | 9/2001 |
| WO | 2004018414 A2 | 3/2004 |
| WO | 2004052852 A1 | 6/2004 |
| WO | 2006033995 A2 | 3/2006 |
| WO | 2008120759 A1 | 10/2008 |
| WO | 2009131065 A1 | 10/2009 |
| WO | 2009158473 A1 | 12/2009 |
| WO | 2010012442 A2 | 2/2010 |
| WO | 2010123139 A1 | 10/2010 |
| WO | 2011008597 A1 | 1/2011 |
| WO | 2011151651 A1 | 12/2011 |
| WO | 2013006394 A1 | 1/2013 |
| WO | 2013096744 A1 | 6/2013 |
| WO | 2013130703 A2 | 9/2013 |
| WO | 2013144129 A1 | 10/2013 |
| WO | 2013163404 A1 | 10/2013 |
| WO | 2013181584 A2 | 12/2013 |
| WO | 2014033170 A1 | 3/2014 |
| WO | 2014106019 A2 | 7/2014 |
| WO | 2014184350 A1 | 11/2014 |
| WO | 2014184365 A1 | 11/2014 |
| WO | 2015005295 A1 | 1/2015 |
| WO | 2015074546 A1 | 5/2015 |
| WO | 2015108631 A1 | 7/2015 |
| WO | 2015109130 A1 | 7/2015 |
| WO | 2015113990 A1 | 8/2015 |
| WO | 2015173164 A1 | 11/2015 |
| WO | 2016016370 A1 | 2/2016 |
| WO | 2016023877 A1 | 2/2016 |
| WO | 2016025933 A2 | 2/2016 |
| WO | 2016071215 A1 | 5/2016 |
| WO | 2016089990 A1 | 6/2016 |
| WO | 2016107832 A1 | 7/2016 |
| WO | 2016128335 A1 | 8/2016 |
| WO | 2016177655 A1 | 11/2016 |
| WO | 2017013046 A1 | 1/2017 |
| WO | 2017017042 A1 | 2/2017 |
| WO | 2017017043 A1 | 2/2017 |
| WO | 2017061466 A1 | 4/2017 |
| WO | 2017136403 A1 | 8/2017 |
| WO | 2017140821 A1 | 8/2017 |
| WO | 2017153919 A1 | 9/2017 |
| WO | 2017155844 A1 | 9/2017 |
| WO | 2017205115 A1 | 11/2017 |
| WO | 2017216391 A1 | 12/2017 |
| WO | 2017216685 A1 | 12/2017 |
| WO | 2017216686 A1 | 12/2017 |
| WO | 2018001944 A1 | 1/2018 |
| WO | 2018001952 A1 | 1/2018 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018083081 A1 | 5/2018 |
| WO | 2018083106 A1 | 5/2018 |
| WO | 2018083136 A1 | 5/2018 |
| WO | 2018085619 A1 | 5/2018 |
| WO | 2018087345 A1 | 5/2018 |
| WO | 2018130152 A1 | 7/2018 |
| WO | 2018144605 A1 | 8/2018 |
| WO | 2018154466 A1 | 8/2018 |
| WO | 2018161960 A1 | 9/2018 |
| WO | 2018181883 A1 | 10/2018 |
| WO | 2018196805 A1 | 11/2018 |
| WO | 2018198079 A1 | 11/2018 |
| WO | 2018219356 A1 | 12/2018 |
| WO | 2019069293 A1 | 4/2019 |
| WO | 2019097479 A1 | 5/2019 |
| WO | 2019100735 A1 | 5/2019 |
| WO | 2019110352 A1 | 6/2019 |
| WO | 2019123285 A1 | 6/2019 |
| WO | 2019129681 A1 | 7/2019 |
| WO | 2019143902 A2 | 7/2019 |
| WO | 2019166951 A1 | 9/2019 |
| WO | 2019206799 A1 | 10/2019 |

(56) References Cited

FOREIGN PATENT DOCUMENTS

WO      2020150366 A1    7/2020
WO      2020190740 A1    9/2020

OTHER PUBLICATIONS

Ho, G. et al., "The SAR development of dihydroimidazoisoquinoline derivates as phosphodiesterase 10A inhibitors for the treatment of schizophrenia", Bioorganic& Medicinal Chemistry Letters, vol. 22, Feb. 9, 2012, 2585-2589.
CAS registry No. 1011646-53-9; Entry Date Apr. 3, 2008.
CAS registry No. 1011895-54-7; Entry Date: Apr. 3, 2008.
CAS registry No. 1011949-47-5; Entry Date: Apr. 3, 2008.
CAS registry No. 1011949-58-8; Entry Date: Apr. 3, 2008.
Chemical Abstract Service STN CAplus [online database], Accession No. 2003:1014580. (Year: 2003).
Chemical Abstract Service STN Database Registry No. 1578268-77-5 [online][Entered STN: Apr. 1, 2014].
Chemical Abstracts Registry No. 1026741-09-2, indexed in the Registry file on Jun. 9, 2008.
Chemical Abstracts Registry No. 115280-56-3, indexed in the Registry file on STN CAS Online Jul. 16, 1988.
Chemical Abstracts Registry No. 1269203-67-9, indexed in the Registry file on STN CAS Online Mar. 21, 2011.
Chemical Abstracts Registry No. 1350251-34-1, indexed in the Registry file on STN CAS Online Dec. 7, 2011.
Chemical Abstracts Registry No. 397288-41-1, indexed in the Registry file on Mar. 1, 2002.
Chemical Abstracts Registry No. 792901-47-4, indexed in the Registry file on STN CAS Online Dec. 6, 2004.
Chemical Abstracts Registry No. 92555-24-3, indexed in the Registry file on Dec. 17, 1984.
Chemical Abstracts Registry No. 950067-32-0, indexed in the Registry file on Oct. 10, 2007.
PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.
PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.
PubChem CI D 10194182, National Center for Biotechnology Information. PubChem Compound Database; CI 0=10194182, https://pubchem.ncbi.nlm.nih.gov/compound/10194182 (accessed May 19, 2017), create date Oct. 25, 2006.
Pubchem, CID 90713021, Create Date: Mar. 16, 2015.
Pubchem—'428' Create Date: Sep. 11, 2005 (Sep. 11, 2005) Date Accessed: Jun. 17, 2016.
Pubchem—CID 23201920, Create Date: Dec. 5, 2007, p. 3.
Pubchem—CID 63186259, Create Date: Oct. 22, 2012 (Oct. 22, 2012) p. 3.
Pubchem—SID 15224030 Deposit Date: Oct. 25, 2006.
Pubchem—57224610 ('610') Create Date: Jun. 14, 2012 (Jun. 14, 2012) Date Accessed: Jun. 17, 2016.
CAS Abstract and Indexed Compounds WO 01/68647 (2001), 2001.
PubChem SID 79456770 CID 10880307, 2009.
"(3'R,4R)-3-[(E)-But-2-enyl]-3'-(2-chloro-4-fluorophenyl)-4'-[1-(difluoromethyl)pyrazol-3-yl]-1'-(1,3-thiazol-2-yl)spiro[1,3-oxazolidine-4,6'-5, 7-dihydro-3H-pyrrolo[1,2-c] pyrimidine]-2-one", PubChem, CID: 138722908, Retrieved from the Internet <URL: https://pubchem.ncbi.nlm.nih.gov/compound/138722908>, Jan. 10, 2019.
"8-Tert-butyl-4-[(1 E)-1-(difluoromethoxy)buta-1,3-dienyl]-5-ethyl-12-oxo-6, 9-diazatricyclo[7.4.0.02,6]trideca-1 (13),2,4, 10-tetraene-11-carboxylic acid", PubChem—CID-134460393, CreateDate: Jun. 23, 2018 (Jun. 23, 2018), p. 2, Fig.
"N-[4-(cyanomethyl)phenyl]-5-(hexyhydro-1-H-azepine-1-yl)sulfonyl]-2-methoxy-benzamid e", Database Registry [Online] Chemical Abstracts Service, Columbus, Ohio, US; May 6, 2011 (May 6, 2011), XP55358935,accession No. RN 1291044-81-9.
Ballatore, C. et al., "Carboxylic Acid (Bio)lsosteres in Drug Design", ChemMedChem., vol. 8, No. 3, 2013, 385-395.
Chowshury, C. et al., "A rapid and facile method for the general synthesis of 3-aryl substituted 4,5,6,7-tetrahydro[1,2,3]triazolo[1,5-a]pyrazines and their ring fused analogues", Organic & Biomolecular Chemistry, vol. 9, 2011, 5856-5862.
Clark, M. T. et al., "5-(alkylsulfonyl)salicylanilides as Potential Dental Antiplaque Agent", Journal of Medicinal Chemistry, 29(1), 1986, 25-29.
Das, J. et al., "Discovery of 2-Amino-heteroaryl-benzothiazole-6-anilides as Potent p56lck Inhibitors", Biorganic & Medicinal Chemistry Letters, 13, 2003, 2587-2590.
El-Hamouly, W. S. et al., "Synthesis and Antimicrobial Activity of New 3, 4-Dihydropyrimidinones", International Journal of Pharmaceutical Sciences and Research, vol. 2, 2011, 1054-1062.
Flachner, B. et al., "Rapid in silico selection of an MCHR1 antagonists' focused library from multi-million compounds' repositories: biological evaluation", Med. Chem. Res., 23, 2014, 1234-1247.
Janetka, J. W. et al., "Discovery of a novel class of 2-ureido thiophene carboxamide checkpoint kinase inhibitors", Bioorganic & Medicinal Chemistry Letters, 18, 2008, 4242-4248.
Li, X. et al., ACS Medicinal Chemistry Letters, 8, 2017, 969-974.
Noguchi, C. et al., "G to A Hypermutation of Hepatitis B Virus", Hepatology, vol. 41, No. 3, 2005, 626-633.
Qiu, Z. et al., "Design and Synthesis of Orally Bioavailable 4-Methyl Heteroaryldihydropyrimidine Based Hepatitis B Virus (HBV) Capsid Inhibitors", Journal of Medicinal Chemistry, 2016.
Schiff, E. et al., "Characterization of the Kinetics of the Pasive and Active Transport Mechanisms for Bile Acid Absorption in the Small Intestine and Colon of the Rat", J. of Clin. Investigation, 51(6), https://doi.org/10.1172/JCI106931, 1972, 1351-1362.
Stachulski, A. V. et al., "Thiazolides as Novel Antiviral Agensts. 1. Inhibition of Hepatistis B Virus Replication", J. Med. Chem., 54, May 9, 2011, 4119-4132.
Teuber, H. et al., "Simple indolo[2,3-a]quinolizine synthesis", Tetrahedron Letters, vol. 5(7), 1964, 325-329.
Wu, et al., Toxicology, 236, 2007, 1-6.
Yang, et al., "Enzyme-mediated hydrolytic activation of prodrugs", Acta Pharmaceutica Sinica B., vol. 1(3), Sep. 9, 2011, 143-159.
Anderson, B. D. et al., "Part VII: Chemical issues on pharmaceutical and formulation, Section 34: Preparation of water-soluble organic compounds by salt formation", The Practice of Medicinal Chemistry, the second volume, Technomics, Inc., 1998, 347-365.
Henderson, E. A. et al., 1,4-Benzodiazepines as Inhibitors of Respiratory Syncytial Virus. The Identification of a Clinical Candidate, Journal of Medicinal Chemistry, 50(7), DOI: http://dx.doi.org/10.1021/jm0607471, Apr. 2007, 1685-1692.
Teuber, H. et al., "Indolo[2,3-a]chinolizine und eine einfache Synthese von Flavoserpentin", Liebigs Ann Chem., 1988(12), DOI: 10.1002/jlac.198819881202, Dec. 14, 1988, 1111-1120.
Patani, G. A. et al., "Bioisosterism: A Rational Approach in Drug Design", Chem. Rev., 96, 1996, 3147-3176.

* cited by examiner

FUNCTIONALIZED HETEROCYCLIC COMPOUNDS AS ANTIVIRAL AGENTS

RELATED APPLICATION

This application claims the benefit of U.S. Provisional Application No. 62/990,118, which was filed on Mar. 16, 2020. The entire teachings of the above application are incorporated herein by reference.

TECHNICAL FIELD

The present invention relates generally to compounds and pharmaceutical compositions useful as hepatitis virus replication inhibitors. Specifically, the present invention relates to tetracyclic pyridone compounds that are useful in treating viral infections such as hepatitis B virus (HBV). The invention provides novel tetracyclic pyridone compounds as disclosed herein, pharmaceutical compositions containing such compounds, and methods of using these compounds and compositions in the treatment and prevention of HBV infections.

BACKGROUND OF THE INVENTION

Over 240 million people throughout the world are chronically infected with hepatitis B virus (HBV). Out of this patient population, at least 2 million reside in the United States. For those that are chronically infected, many will develop complications of liver disease from cirrhosis or hepatocellular carcinoma (HCC).

HBV is a member of the Hepadnavirus family, and it is able to replicate through the reverse transcription of an RNA intermediate. The 3.2-kb HBV genome exists in a circular, partially doublestranded DNA conformation (rcDNA) that has four overlapping open reading frames (ORF). These encode for the core, polymerase, envelope, and X proteins of the virus. rcDNA must be converted into covalently closed circular DNA (cccDNA) in cells prior to the transcription of viral RNAs. As rcDNA is transcriptionally inert, cccDNA is the only template for HBV transcription, and its existence is required for infection.

The HBV viral envelope contains a mixture of surface antigen proteins (HBsAg). The HBsAg coat contains three proteins that share a common region that includes the smallest of the three proteins (SHBsAg). The other two proteins, Medium HBsAg (MHBsAg) and Large HBsAg (LHBsAg), both contain a segment of SHBsAg with additional polypeptide segments. SHBsAg, MHBsAg, and LHBsAg can also assemble into a non-infectious subviral particle known as the 22-nm particle that contains the same proteins found around infectious viral particles. As the 22-nm particles contain the same antigenic surface proteins that exist around the infectious HBV virion, they can be used as a vaccine to produce neutralizing antibodies.

In chronically infected patients, the non-infectious 22-nm particles are found in much greater abundance than the infectious virions. As a result, the 22-nm particles are thought to be able to protect the infectious virions from the infected host's immune response. Not only can they serve as infectious decoys, but they also suppress normal functioning of immune cells thereby impairing the host's immune response to HBV. Therefore, reducing the level of subviral particles is a feasible therapeutic approach to treating HBV infections. (Refer to WO2015/13990).

In the clinical setting, a diagnostic marker of chronic HBV infection is high serum levels of HBsAg. In recent years, data have suggested that sustained virologic response (SVR) corresponds with HBsAg decline during early treatment, while sustained exposure to HBsAg and other viral antigens might lead to inept immunogenicity. Patients that display higher decreases in serum HBsAg reached a considerably higher SVR following treatment.

Current treatment options for chronically infected HBV patients are limited in number and scope. They include interferon therapy and nucleoside-based inhibitors of HBV DNA polymerase, namely entecavir and tenofovir. The current standard of care is dedicated to reducing the level of viremia and allowance of liver dysfunction, but is associated with negative side-effects and increase persistence of drug-resistant HBV mutants. A significant shortcoming of current therapies is that they are unable to eliminate hepatic reservoirs of cccDNA, prevent transcription of HBsAg from cccDNA, or limit the secretion of HBsAg into serum that will ultimately stifle the immune response. Although compounds have been reported to reduce serum HBsAg levels, they have not been approved as HBV therapies. (Refer to WO2015/113990, WO2015/173164, WO2016/023877, WO2016/071215, WO2016/128335, WO 2017/140821, WO2019097479, WO2019166951, WO2019123285, WO2018198079, WO2018073753, WO2018047109, WO2019110352, WO2019129681, WO2018087345, WO2018083136, WO2018083106, WO2018083081, WO2017216391, WO2018001952, WO2018001944, WO2016107832, WO2016177655, WO2017017042, WO2017017043, WO2017013046, WO2018219356, WO2018130152, WO2018154466, WO2019069293, WO2017061466, WO2018181883, WO2018161960, WO2017205115, WO2018144605, WO2018085619, WO2018019297, and WO2018022282).

More effective therapies for chronic HBV infections are needed due to this high unmet clinical need. This invention describes the methods to prepare and methods for use of compounds that are believed to suppress the secretion of subviral particles containing HBsAg. Compounds of this type might be used to treat HBV infections and decrease occurrence of liver disease complications such as cirrhosis or HCC.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention provides processes for the preparation of said compounds.

The present invention provides compounds represented by Formula (I),

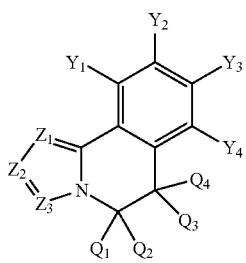

and pharmaceutically acceptable salts, N-oxides, esters and prodrugs thereof, wherein:

$Q_1$, $Q_2$, $Q_3$, and $Q_4$ are each independently selected from hydrogen, halo, —$NR_{11}R_{12}$, optionally substituted —$C_1$-$C_6$ alkyl, optionally substituted —$C_2$-$C_6$ alkenyl, optionally substituted —$C_1$-$C_6$ alkoxy, optionally substituted —$C_3$-$C_8$ cycloalkyl; optionally substituted —$C_3$-$C_8$ cycloalkenyl; optionally substituted 3- to 8-membered heterocycloalkyl; optionally substituted aryl; and optionally substituted heteroaryl;

$Y_1$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —C(O)$R_{11}$; —C(O)O$R_{11}$; —C(O)N($R_{11}$)($R_{12}$); —C(O)N($R_{11}$)S(O)$_2$($R_{12}$); —O$R_{11}$, —N$R_{11}R_{12}$; —S$R_{11}$; —S(O)$_2R_{11}$; or —S(O)$_2$N($R_{11}$)($R_{12}$);

$Y_2$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —C(O)$R_{11}$; —C(O)O$R_{11}$; —C(O)N($R_{11}$)($R_{12}$); —C(O)N($R_{11}$)S(O)$_2$($R_{12}$); —O$R_{11}$, —N$R_{11}R_{12}$; —S$R_{11}$; —S(O)$_2R_{11}$; —S(O)$_2$N($R_{11}$)($R_{12}$), or —O—Si($R_{11}$)$_3$;

$Y_3$ is —C(O)$R_{11}$, —COO$R_{11}$, —C(O)NHSO$_2R_{11}$, —C(O)NHSO$_2$N$R_{11}R_{12}$, or 1,2,4-oxadiazol-3-yl-5(4H)-one, or $Y_3$ is optionally substituted aryl, optionally substituted heteroaryl, optionally substituted —$C_5$-$C_6$ cycloalkyl, or optionally substituted 5- to 6-membered heterocycloalkyl;

$Y_4$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —C(O)$R_{11}$; —C(O)O$R_{11}$; —C(O)N($R_{11}$)($R_{12}$); —C(O)N($R_{11}$)S(O)$_2$($R_{12}$); —O$R_{11}$, —N$R_{11}R_{12}$; —S$R_{11}$; —S(O)$_2R_{11}$; or —S(O)$_2$N($R_{11}$)($R_{12}$);

Alternatively, $Y_2$ and $Y_3$ are taken together to form an optionally substituted 5-12 membered heterocyclic ring or carbocyclic ring containing 1, 2, or 3 double bonds;

$Z_1$ is N or $CR_1$, $Z_2$ is N or $CR_2$, and $Z_3$ is N or $CR_3$; in certain embodiments, at least one of $Z_1$, $Z_2$ and $Z_3$ is N;

$R_1$, $R_2$ and $R_3$ are each independently selected from:
1) hydrogen;
2) halogen;
3) —NO$_2$;
4) Cyano;
5) Optionally substituted —$C_1$-$C_8$ alkyl;
6) Optionally substituted —$C_2$-$C_8$ alkenyl;
7) Optionally substituted —$C_2$-$C_8$ alkynyl;
8) Optionally substituted —$C_3$-$C_8$ cycloalkyl;
9) Optionally substituted 3- to 12-membered heterocycloalkyl;
10) Optionally substituted aryl;
11) Optionally substituted arylalkyl;
12) Optionally substituted heteroaryl;
13) Optionally substituted heteroarylalkyl;
14) —S$R_{11}$;
15) —S(O)$_2R_{11}$;
16) —S(O)$_2$N($R_{11}$)($R_{12}$);
17) —C(O)$R_{11}$;
18) —C(O)O$R_{11}$;
19) —C(O)N($R_{11}$)($R_{12}$);
20) —C(O)N($R_{11}$)S(O)$_2$($R_{12}$);
21) —N($R_{11}$)($R_{12}$);
22) —N($R_{13}$)C(O)N($R_{11}$)($R_{12}$);
23) —N($R_{11}$)C(O)($R_{12}$);
24) —N($R_{11}$)C(O)$_2$($R_{12}$);
25) —N($R_{13}$)S(O)$_2$N($R_{11}$)($R_{12}$);
26) —N($R_{11}$)S(O)$_2$($R_{12}$);
27) —O$R_{11}$;
28) —OC(O)$R_{11}$;
29) —OC(O)O$R_{11}$; and
30) —OC(O)N($R_{11}$)($R_{12}$);

wherein $R_{11}$, $R_{12}$, and $R_{13}$, are each independently selected from hydrogen, optionally substituted —$C_1$-$C_8$ alkyl, optionally substituted —$C_2$-$C_8$ alkenyl, optionally substituted —$C_3$-$C_8$ cycloalkyl, optionally substituted 3- to 8-membered heterocycloalkyl, optionally substituted aryl, and optionally substituted heteroaryl. Alternatively, $R_{11}$ and $R_{12}$ are taken together with the nitrogen atom to which they attached to form an optionally substituted 3-8 membered heterocyclic containing 0, 1, 2, or 3 double bonds.

Preferably, $R_2$ is optionally substituted aryl, optionally substituted heteroaryl or optionally substituted bicyclic heterocycloalkyl, more preferably optionally substituted aryl or optionally substituted heteroaryl.

Preferably $R_1$ is optionally substituted aryl, optionally substituted heteroaryl, optionally substituted —$C_3$-$C_8$ cycloalkyl or optionally substituted 3- to 12-membered heterocycloalkyl; and $R_2$ is optionally substituted aryl, optionally substituted heteroaryl, optionally substituted —$C_3$-$C_8$ cycloalkyl or optionally substituted 3- to 12-membered heterocycloalky.

In certain embodiments, $Z_3$ is N, $Z_1$ is $CR_1$ and $Z_2$ is $CR_2$, and $R_2$ is not hydrogen; halogen; cyano; optionally substituted —$C_1$-$C_6$ alkyl; optionally substituted —$C_3$-$C_7$ cycloalkyl; optionally substituted 3- to 7-membered heterocycloalkyl; —NH$_2$; —NH$C_1$-$C_6$ alkyl; —OH; or —O$C_1$-$C_6$ alkyl. In this embodiment, $R_2$ is preferably optionally substituted aryl, optionally substituted heteroaryl, optionally substituted arylalkyl, or optionally substituted heteroarylalkyl, and $R_1$ is preferably optionally substituted aryl, optionally substituted arylalkyl, optionally substituted heteroaryl, optionally substituted heteroarylalkyl, hydrogen or halogen.

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

In certain embodiments, the present invention relates to compounds of Formula (I), and pharmaceutically acceptable salts thereof, wherein $Y_1$ is hydrogen, F, Cl, —NH$_2$, —CH$_3$, —CHF$_2$, —CF$_3$, —OCH$_3$, or optionally substituted cyclopropyl.

In certain embodiments, the present invention relates to compounds of Formula (I), and pharmaceutically acceptable salts thereof, wherein $Y_2$ is F, Cl, —NH$_2$, —CH$_3$, —CHF$_2$, —CF$_3$, or —OCH$_3$.

In certain embodiments, the present invention relates to compounds of Formula (I), and pharmaceutically acceptable salts thereof, wherein $Y_2$ is —OH.

In certain embodiments, the present invention relates to compounds of Formula (I), and pharmaceutically acceptable salts thereof, wherein $Y_3$ is —COOH, —C(O)NHSO$_2$NR$_{11}$R$_{12}$, wherein R$_{11}$ and R$_{12}$ are as previously defined or $Y_3$ is triazolyl.

In certain embodiments, the present invention relates to compounds of Formula (I), and pharmaceutically acceptable salts thereof, wherein $Y_4$ is hydrogen, —OH, or —CH$_3$.

In certain embodiments, the present invention relates to compounds of Formula (I), and pharmaceutically acceptable salts thereof, wherein at least one of R$_1$, R$_2$ and R$_3$, preferably R$_2$, is optionally substituted aryl; optionally substituted arylalkyl; optionally substituted heteroaryl; or optionally substituted heteroarylalkyl.

In certain embodiments, $Z_3$ is N, $Z_2$ is CR$_2$, and $Z_1$ is CR$_1$, wherein R$_1$ and R$_2$ are as defined above. In certain embodiments, R$_1$ is hydrogen or halogen, preferably hydrogen. In certain embodiments, R$_2$ is optionally substituted aryl; optionally substituted arylalkyl; optionally substituted heteroaryl; or optionally substituted heteroarylalkyl.

In certain embodiments, $Z_3$ is N, $Z_1$ is CR$_1$, and $Z_2$ is CR$_2$, wherein R$_1$ is optionally substituted aryl, optionally substituted arylalkyl, optionally substituted heteroaryl, optionally substituted heteroarylalkyl, optionally substituted —C$_3$-C$_8$ cycloalkyl, or optionally substituted 3- to 12-membered heterocycloalkyl; and R$_2$ is as previously defined. Preferably, R$_1$ is optionally substituted aryl, optionally substituted heteroaryl, optionally substituted —C$_3$-C$_8$ cycloalkyl, or optionally substituted 3- to 8-membered heterocycloalkyl; and R$_2$ is as previously defined. More preferably, R$_1$ is optionally substituted aryl, optionally substituted heteroaryl, optionally substituted —C$_3$-C$_8$ cycloalkyl, or optionally substituted 3- to 8-membered heterocycloalkyl; and R$_2$ is hydrogen.

In certain embodiments, $Z_3$ is N, $Z_1$ is CR$_1$, and $Z_2$ is CR$_2$, wherein R$_2$ is optionally substituted aryl, optionally substituted arylalkyl, optionally substituted heteroaryl, optionally substituted heteroarylalkyl, optionally substituted —C$_3$-C$_8$ cycloalkyl, or optionally substituted 3- to 12-membered heterocycloalkyl; and R$_1$ is as previously defined. Preferably, R$_2$ is optionally substituted aryl, optionally substituted heteroaryl, optionally substituted —C$_3$-C$_8$ cycloalkyl, or optionally substituted 3- to 8-membered heterocycloalkyl; and R$_1$ is as previously defined. More preferably, R$_2$ is optionally substituted aryl, optionally substituted heteroaryl, optionally substituted —C$_3$-C$_8$ cycloalkyl, or optionally substituted 3- to 8-membered heterocycloalkyl; and R$_1$ is hydrogen.

In certain embodiments, $Z_3$ is N, $Z_1$ is CR$_1$, and $Z_2$ is CR$_2$, wherein R$_1$ is optionally substituted aryl, optionally substituted arylalkyl, optionally substituted heteroaryl, optionally substituted heteroarylalkyl, optionally substituted —C$_3$-C$_8$ cycloalkyl, or optionally substituted 3- to 12-membered heterocycloalkyl; and R$_2$ is optionally substituted aryl, optionally substituted arylalkyl, optionally substituted heteroaryl, optionally substituted heteroarylalkyl, optionally substituted —C$_3$-C$_8$ cycloalkyl, or optionally substituted 3- to 12-membered heterocycloalkyl. Preferably, R$_1$ is optionally substituted aryl, optionally substituted heteroaryl, optionally substituted —C$_3$-C$_8$ cycloalkyl, or optionally substituted 3- to 8-membered heterocycloalkyl; and R$_2$ is optionally substituted aryl, optionally substituted heteroaryl, optionally substituted —C$_3$-C$_8$ cycloalkyl, or optionally substituted 3- to 8-membered heterocycloalkyl. More preferably, R$_1$ is optionally substituted aryl or optionally substituted heteroaryl; and R$_2$ is optionally substituted aryl or optionally substituted heteroaryl.

In certain embodiments, the present invention relates to compounds of Formula (I), and pharmaceutically acceptable salts thereof, wherein at least one of R$_1$, R$_2$ and R$_3$, preferably at least one of R$_1$ and R$_2$, is derived from one of the following by removal of a hydrogen atom:

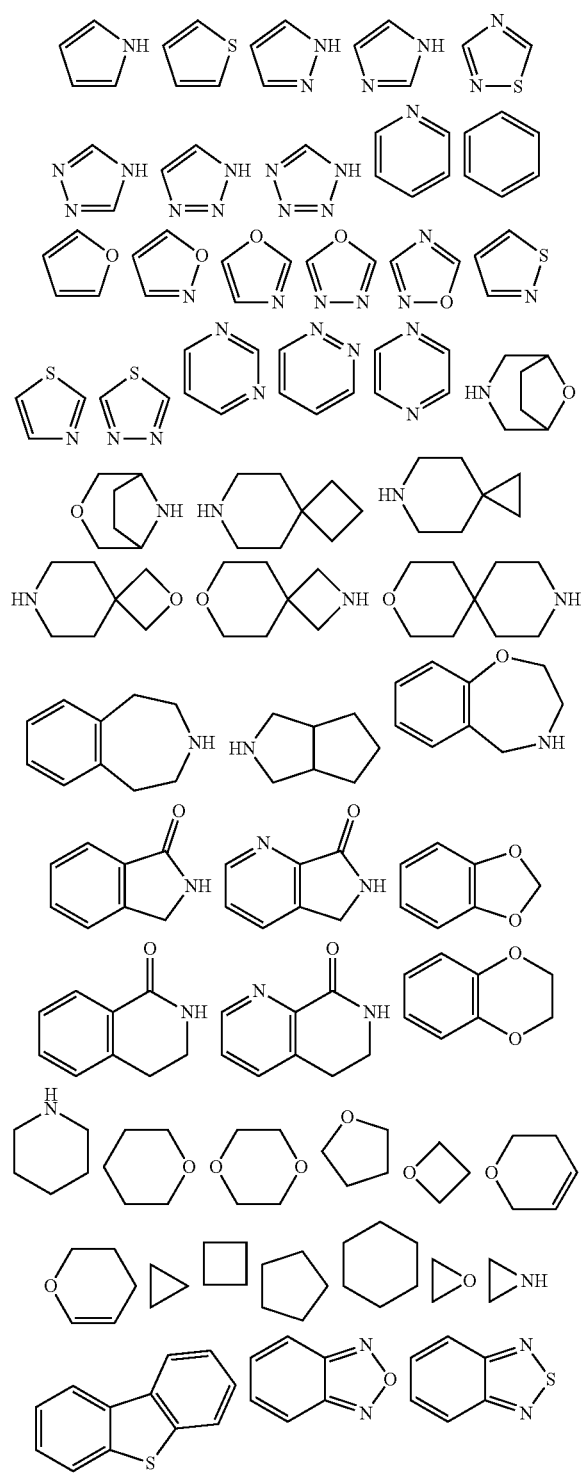

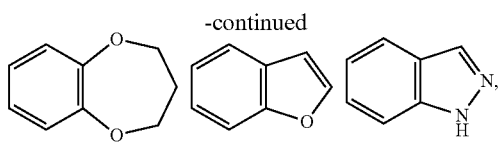

wherein each of these groups is optionally substituted with one to four groups selected from halo, CN, —OR$_{11}$, —NR$_{11}$R$_{12}$, optionally substituted C$_1$-C$_6$ alkyl, and optionally substituted 3- to 8-membered heterocyclic.

In certain embodiments, the present invention relates to compounds of Formula (I), and pharmaceutically acceptable salts thereof, wherein at least one of R$_1$, R$_2$ and R$_3$, preferably at least one of R$_1$ and R$_2$, is selected from one of the following:

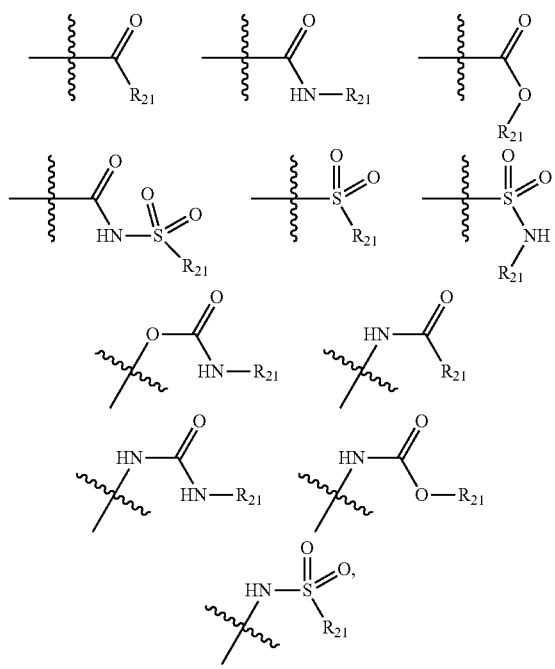

wherein each R$_{21}$ is independently selected from —CH$_3$, -isopropyl, -t-butyl, or one of the following by removal of a hydrogen atom:

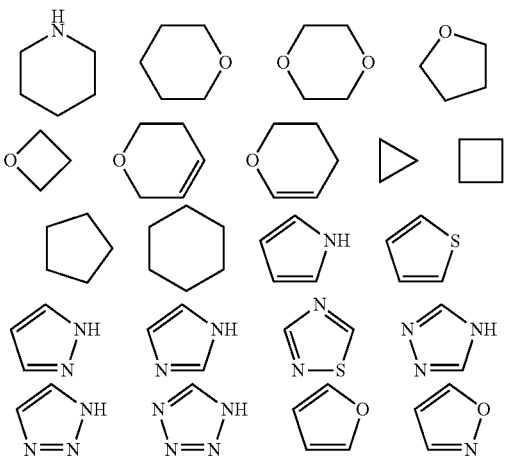

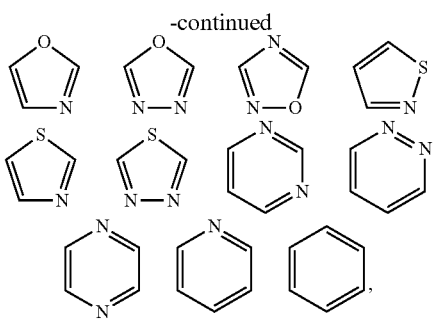

wherein each of these groups is optionally substituted with one to four groups selected from halo, CN, —OR$_{11}$, —NR$_{11}$R$_{12}$, optionally substituted C$_1$-C$_6$ alkyl, and optionally substituted 3- to 8-membered heterocyclic.

In certain embodiments, the present invention relates to compounds of Formula (I), and pharmaceutically acceptable salts thereof, wherein Q$_1$ is hydrogen, Cl or F; Q$_2$ is hydrogen, Cl or F; Q$_3$ is optionally substituted C$_1$-C$_6$ alkyl, hydrogen, Cl or F and Q$_4$ is optionally substituted C$_1$-C$_6$ alkyl, hydrogen, Cl or F.

In certain embodiments, the present invention relates to compounds of Formula (I), and pharmaceutically acceptable salts thereof, wherein Q$_1$ is hydrogen; Q$_2$ is hydrogen; Q$_3$ is optionally substituted C$_1$-C$_6$ alkyl or hydrogen, and Q$_4$ is optionally substituted C$_1$-C$_6$ alkyl or hydrogen.

In certain embodiments, the present invention relates to compounds of Formula (I), and pharmaceutically acceptable salts thereof, wherein Q$_4$ is -t-butyl or isopropyl.

In certain embodiments, the compound of Formula (I) is represented by one of Formulae (II-1)~(II-8), or a pharmaceutically acceptable salt thereof:

(II-1)

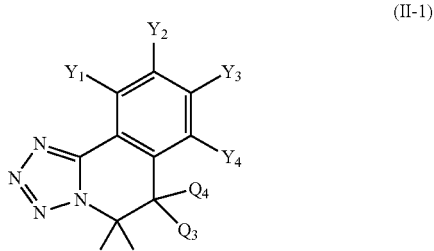

(II-2)

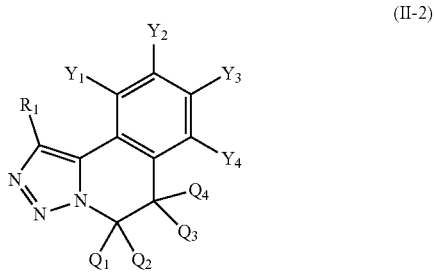

(II-3)

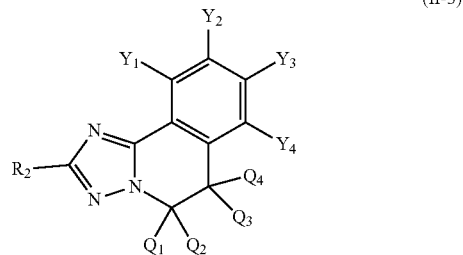

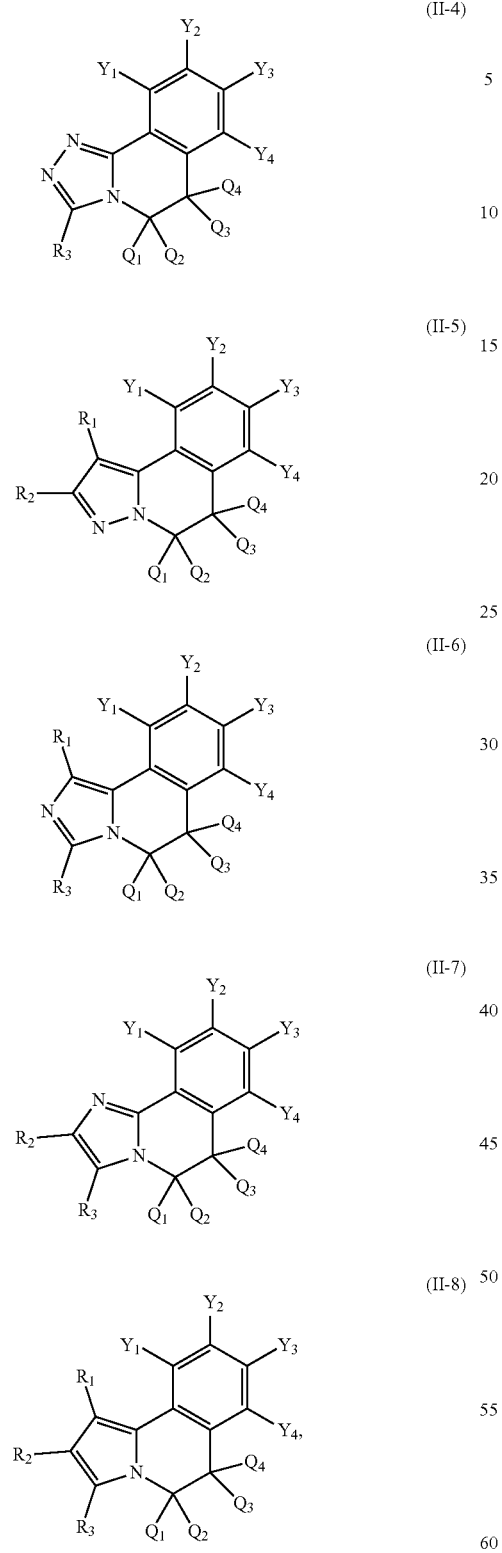
wherein $Y_1$, $Y_2$, $Y_3$, $Y_4$, $R_1$, $R_2$, $R_3$, $Q_1$, $Q_2$, $Q_3$, and $Q_4$ are as previously defined.
In another embodiment, the compound of Formula (I) is represented by one of Formulae (III-1)~Formulae (III-8), or a pharmaceutically acceptable salt thereof:
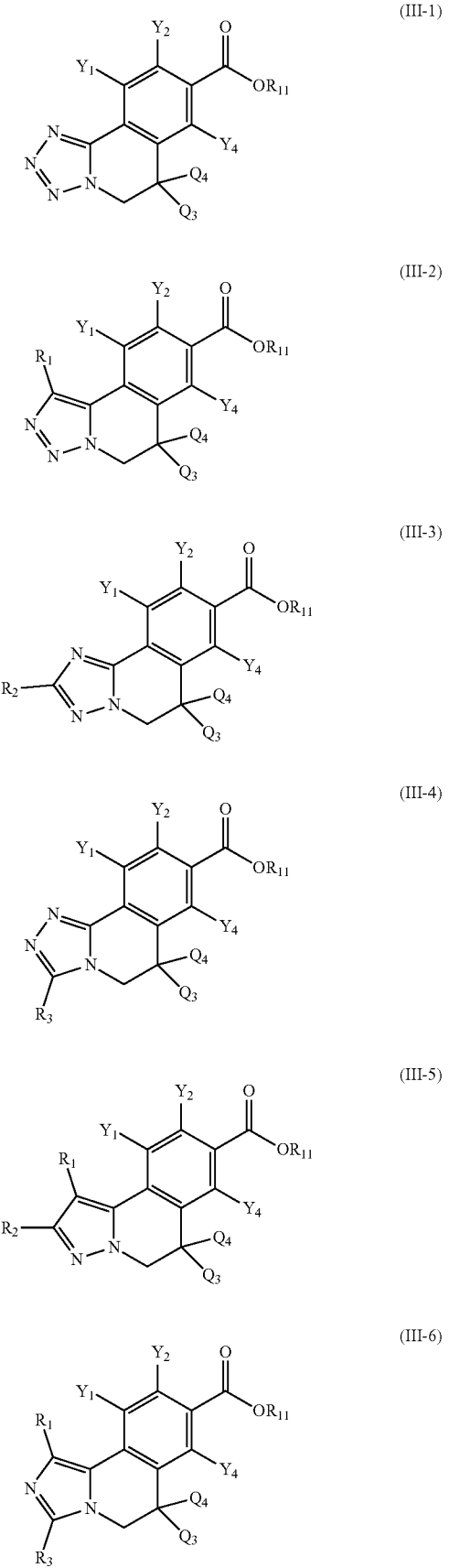

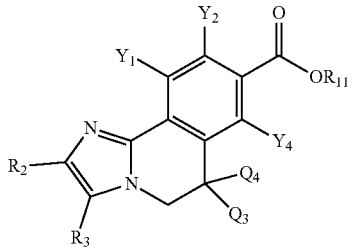
(III-7)

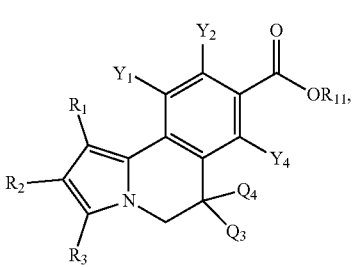
(III-8)

wherein $Y_1$, $Y_2$, $Y_4$, $R_1$, $R_2$, $R_3$, $R_{11}$, $Q_3$ and $Q_4$ are as previously defined.

In another embodiment, the compound of Formula (I) is represented by one of Formulae (III-1a)~Formulae (III-8a), or a pharmaceutically acceptable salt thereof:

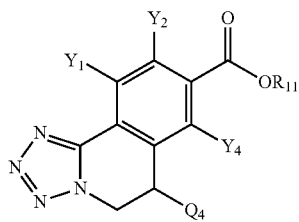
(III-1a)

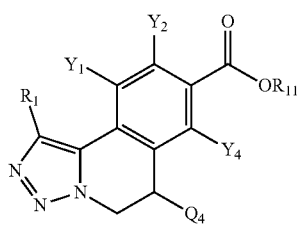
(III-2a)

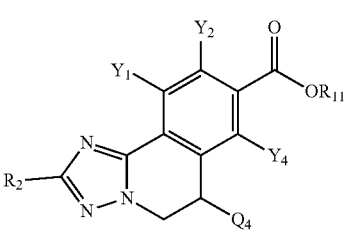
(III-3a)

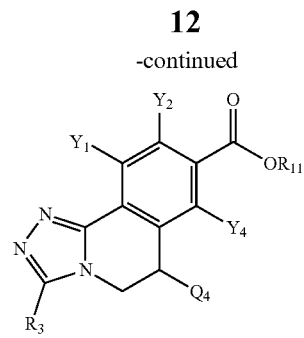
(III-4a)

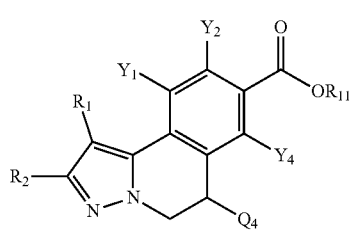
(III-5a)

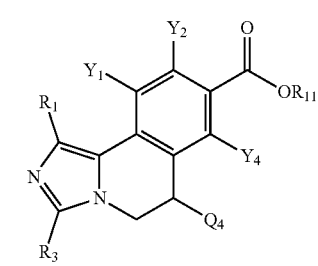
(III-6a)

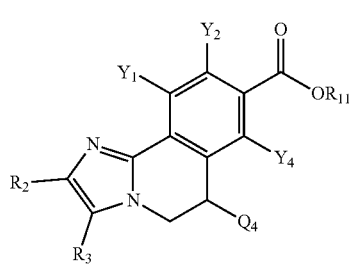
(III-7a)

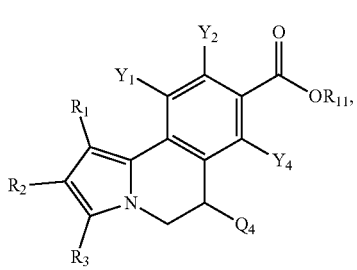
(III-8a)

wherein $Y_1$, $Y_2$, $Y_4$, $R_1$, $R_2$, $R_3$, $R_{11}$, and $Q_4$ are as previously defined.

In another embodiment, the compound of Formula (I) is represented by Formula (IV-1) or Formula (IV-2), or a pharmaceutically acceptable salt thereof:

(IV-1)

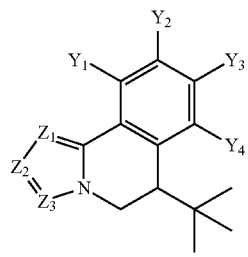

(IV-2)

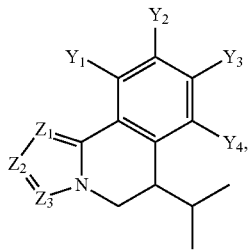

wherein $Y_1$, $Y_2$, $Y_3$, $Y_4$, $Z_1$, $Z_2$, and $Z_3$ are as previously defined.

In another embodiment, the compound of Formula (I) is represented by Formula (IV-1a) or Formula (IV-2a), or a pharmaceutically acceptable salt thereof:

(IV-1a)

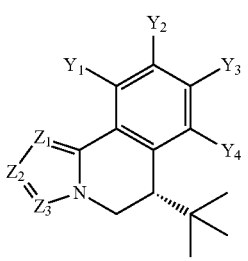

(IV-2a)

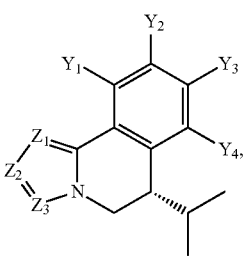

wherein $Y_1$, $Y_2$, $Y_3$, $Y_4$, $Z_1$, $Z_2$, and $Z_3$ are as previously defined.

In another embodiment, the compound of Formula (I) is represented by one of Formulae (V-1)~Formulae (V-8), or a pharmaceutically acceptable salt thereof:

(V-1)

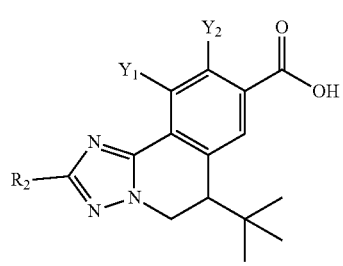

-continued (V-2)

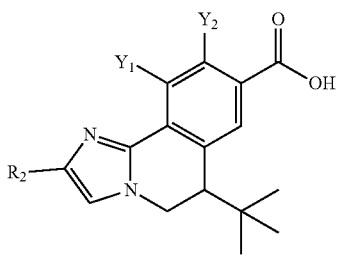

(V-3)

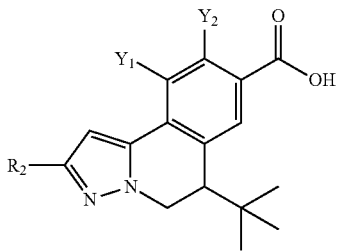

(V-4)

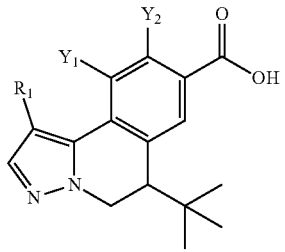

(V-5)

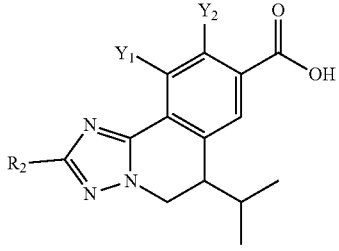

(V-6)

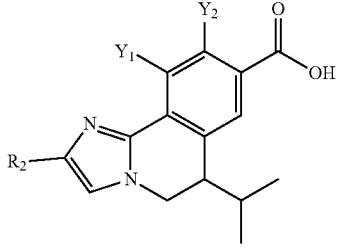

(V-7)

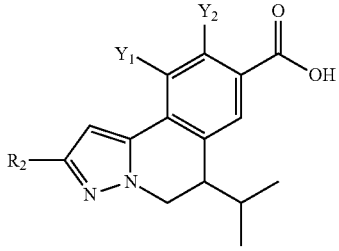

-continued

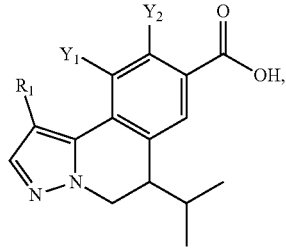
(V-8)

wherein Y₁, Y₂, R₁, and R₂ are as previously defined. Preferably, R₁ is optionally substituted aryl, optionally substituted heteroaryl, optionally substituted —C₃-C₈ cycloalkyl, or optionally substituted 3- to 8-membered heterocycloalkyl; and R₂ is optionally substituted aryl, optionally substituted heteroaryl, optionally substituted —C₃-C₈ cycloalkyl, or optionally substituted 3- to 8-membered heterocycloalkyl.

In another embodiment, the compound of Formula (I) is represented by one of Formulae (VI-1)~Formulae (VI-8), or a pharmaceutically acceptable salt thereof:

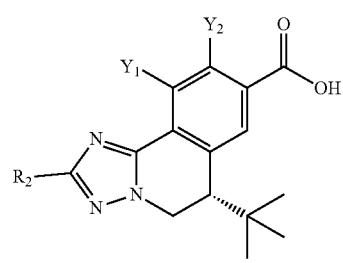
(VI-1)

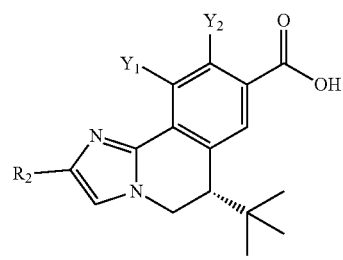
(VI-2)

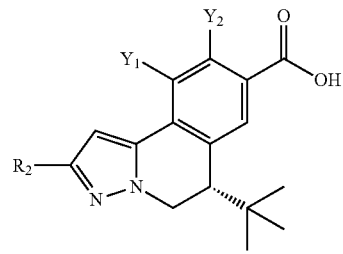
(VI-3)

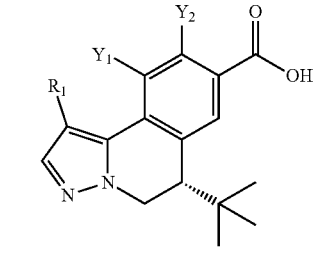
(VI-4)

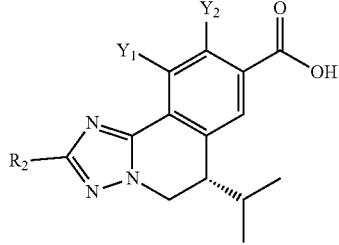
(VI-5)

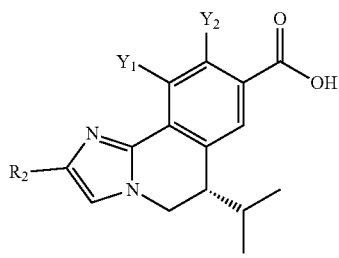
(VI-6)

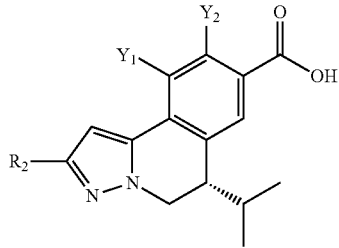
(VI-7)

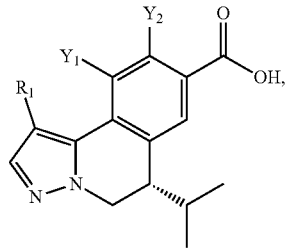
(VI-8)

wherein Y₁, Y₂, R₁, and R₂ are as previously defined. Preferably, R₁ is optionally substituted aryl, optionally substituted heteroaryl, optionally substituted —C₃-C₈ cycloalkyl, or optionally substituted 3- to 8-membered heterocycloalkyl; and R₂ is optionally substituted aryl, optionally substituted heteroaryl, optionally substituted —C₃-C₈ cycloalkyl, or optionally substituted 3- to 8-membered heterocycloalkyl.

In another embodiment, the compound of Formula (I) is represented by one of Formulae (VII-1a)~Formulae (VII-8a), or a pharmaceutically acceptable salt thereof:

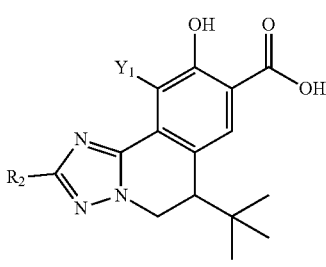
(VII-1a)

(VII-2a) 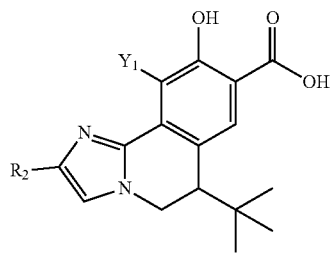

(VII-3a) 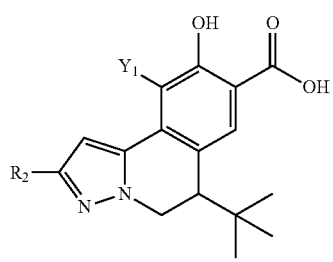

(VII-4a) 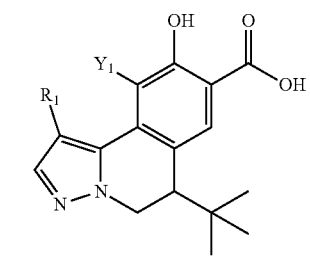

(VII-5a) 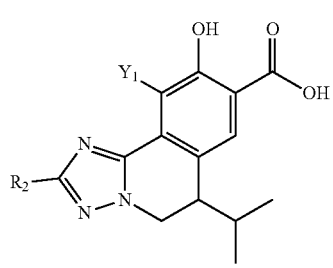

(VII-6a) 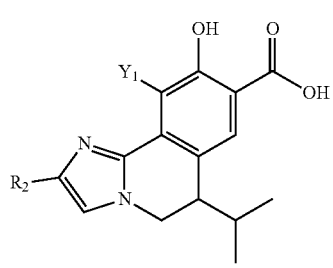

(VII-7a) 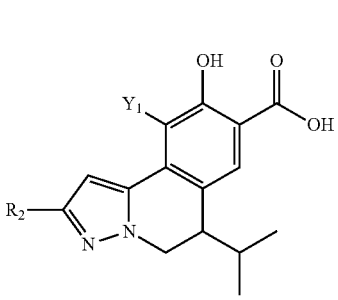

(VII-8a) 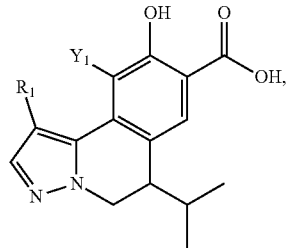

wherein $Y_1$, $R_1$, and $R_2$ are as previously defined. Preferably, $R_1$ is optionally substituted aryl, optionally substituted heteroaryl, optionally substituted —$C_3$-$C_8$ cycloalkyl, or optionally substituted 3- to 8-membered heterocycloalkyl; and $R_2$ is optionally substituted aryl, optionally substituted heteroaryl, optionally substituted —$C_3$-$C_8$ cycloalkyl, or optionally substituted 3- to 8-membered heterocycloalkyl.

In another embodiment, the compound of Formula (I) is represented by one of Formulae (VII-1)~Formulae (VII-8), or a pharmaceutically acceptable salt thereof:

(VII-1) 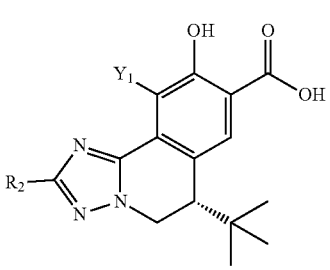

(VII-2) 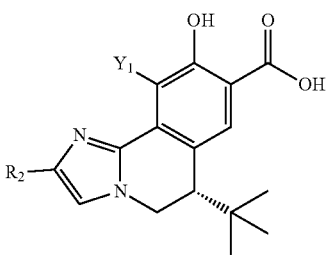

(VII-3) 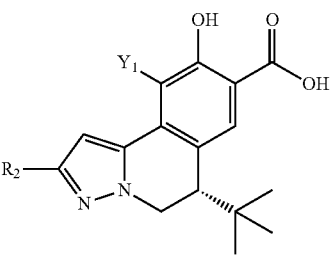

(VII-4) 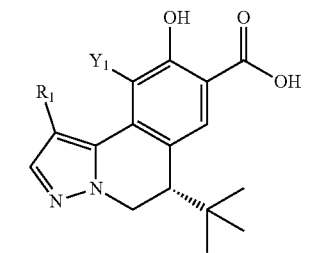

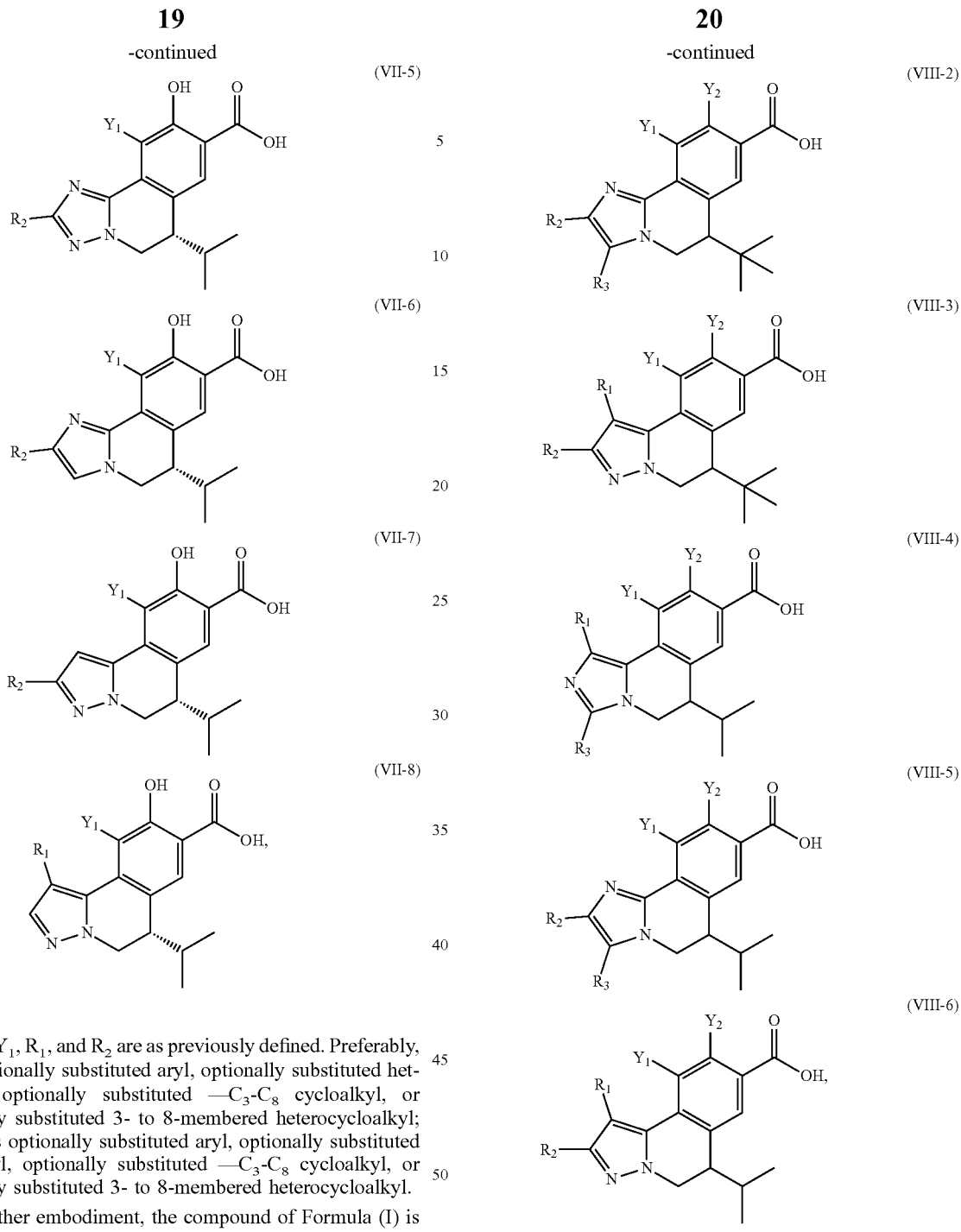

wherein $Y_1$, $R_1$, and $R_2$ are as previously defined. Preferably, $R_1$ is optionally substituted aryl, optionally substituted heteroaryl, optionally substituted —$C_3$-$C_8$ cycloalkyl, or optionally substituted 3- to 8-membered heterocycloalkyl; and $R_2$ is optionally substituted aryl, optionally substituted heteroaryl, optionally substituted —$C_3$-$C_8$ cycloalkyl, or optionally substituted 3- to 8-membered heterocycloalkyl.

In another embodiment, the compound of Formula (I) is represented by one of Formulae (VIII-1)~(VIII-6), or a pharmaceutically acceptable salt thereof:

wherein $Y_1$, $Y_2$, $R_1$, $R_2$, and $R_3$ are as previously defined. Preferably $R_1$, $R_2$, and $R_3$ are each independently selected from hydrogen, halogen, optionally substituted aryl, optionally substituted arylalkyl, optionally substituted heteroaryl, optionally substituted heteroarylalkyl, optionally substituted —$C_3$-$C_8$ cycloalkyl, and optionally substituted 3- to 8-membered heterocycloalkyl. More preferably, $Y_1$ is H, F or cycloproply; $Y_2$ is —OH; and $R_1$, $R_2$, and $R_3$ are each independently selected from optionally substituted aryl and optionally substituted heteroaryl.

In another embodiment, the compound of Formula (I) is represented by one of Formulae (IX-1)~(IX-6), or a pharmaceutically acceptable salt thereof:

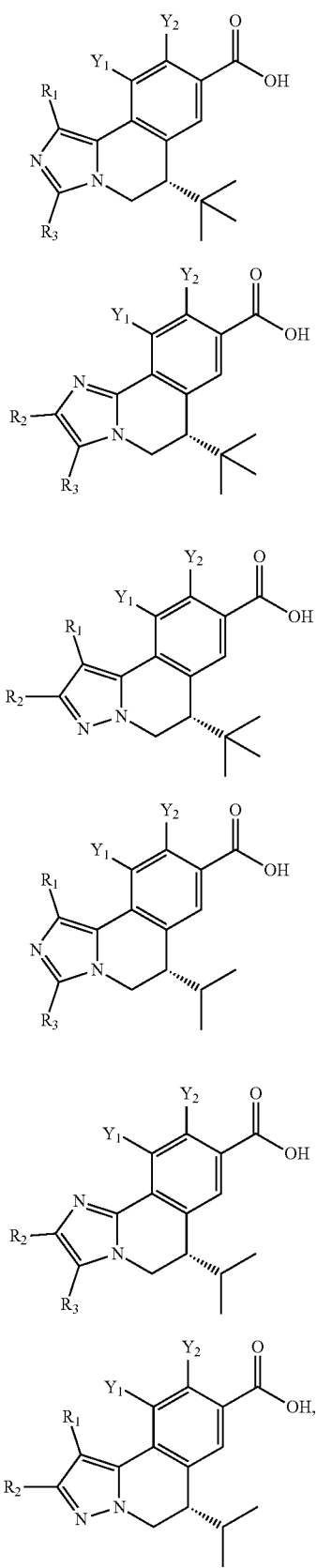

from hydrogen, halogen, optionally substituted aryl, optionally substituted arylalkyl, optionally substituted heteroaryl, optionally substituted heteroarylalkyl, optionally substituted —$C_3$-$C_8$ cycloalkyl, and optionally substituted 3- to 8-membered heterocycloalkyl. More preferably, $Y_1$ is H, F, or cycloproply; $Y_2$ is —OH; and $R_1$, $R_2$, and $R_3$ are each independently selected from optionally substituted aryl and optionally substituted heteroaryl.

In another embodiment, the compound of Formula (I) is represented by one of Formulae (X-1)~(X-6), or a pharmaceutically acceptable salt thereof:

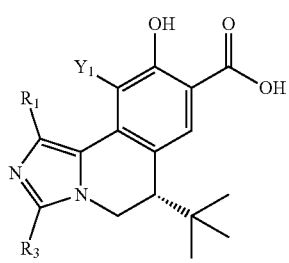

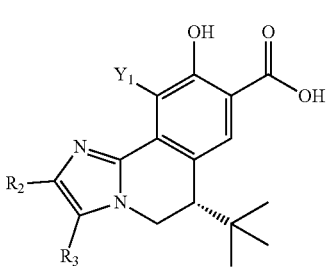

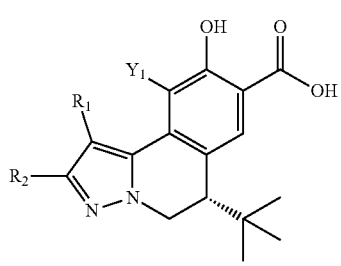

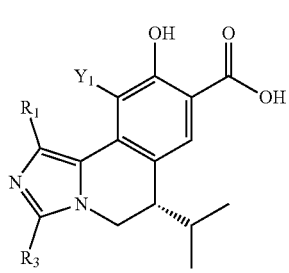

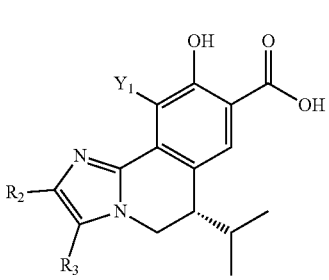

wherein $Y_1$, $Y_2$, $R_1$, $R_2$, and $R_3$ are as previously defined. Preferably $R_1$, $R_2$, and $R_3$ are each independently selected -continued

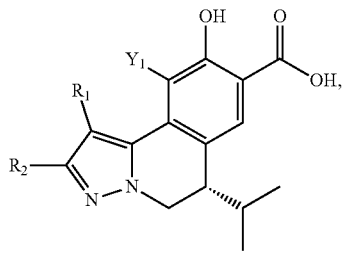
(X-6)

wherein $Y_1$, $R_1$, $R_2$, and $R_3$ are as previously defined. Preferably $R_1$, $R_2$, and $R_3$ are each independently selected from hydrogen, halogen, optionally substituted aryl, optionally substituted arylalkyl, optionally substituted heteroaryl, optionally substituted heteroarylalkyl, optionally substituted —$C_3$-$C_8$ cycloalkyl, and optionally substituted 3- to 8-membered heterocycloalkyl. More preferably, $Y_1$ is H, F, or cycloproply; and $R_1$, $R_2$, and $R_3$ are each independently selected from optionally substituted aryl and optionally substituted heteroaryl.

In another embodiment, the compound of Formula (I) is represented by one of Formulae (XI-1)~(XI-8), or a pharmaceutically acceptable salt thereof:

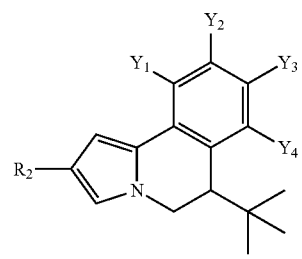
(XI-1)

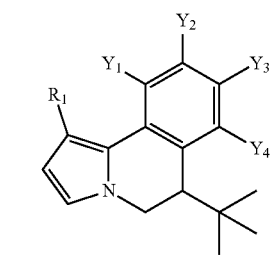
(XI-2)

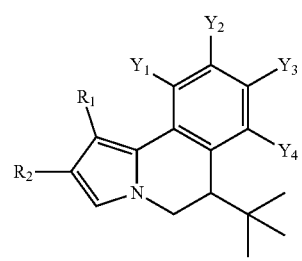
(XI-3)

-continued

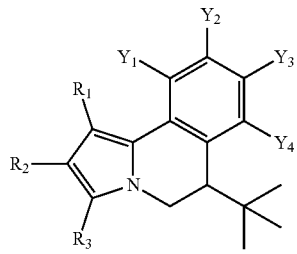
(XI-4)

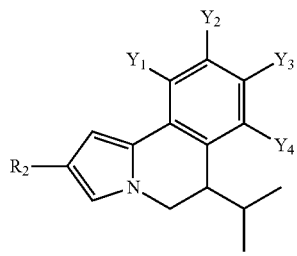
(XI-5)

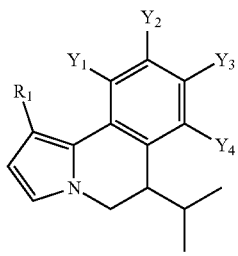
(XI-6)

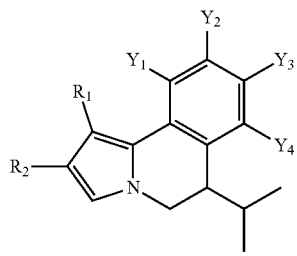
(XI-7)

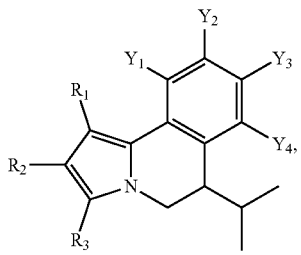
(XI-8)

wherein $Y_1$, $Y_2$, $Y_3$, $Y_4$, $R_1$, $R_2$ and $R_3$ are as previously defined and $R_1$, $R_2$ and $R_3$ are not hydrogen. Preferably, $Y_1$ is H, F or cycloproply; $Y_2$ is —OH; $Y_3$ is —COOR$_{11}$; $Y_4$ is hydrogen; and $R_1$, $R_2$, and $R_3$ are each independently selected from optionally substituted aryl and optionally substituted heteroaryl.

In another embodiment, the compound of Formula (I) is represented by one of Formulae (XII-1)~(XII-8), or a pharmaceutically acceptable salt thereof:

(XII-1) 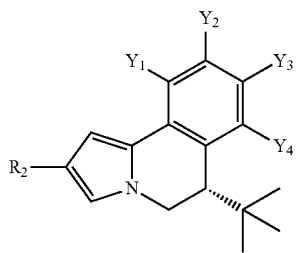

(XII-2) 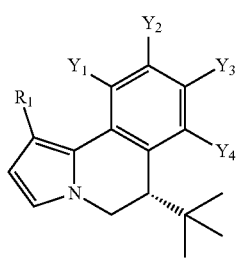

(XII-3) 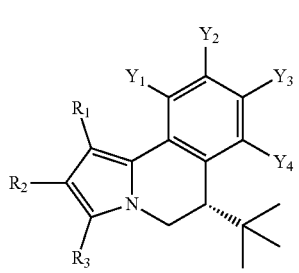

(XII-4) 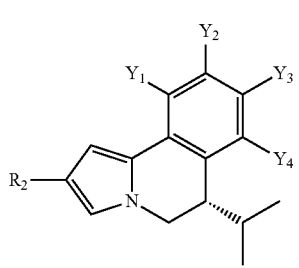

(XII-5)

(XII-6)

(XII-7) 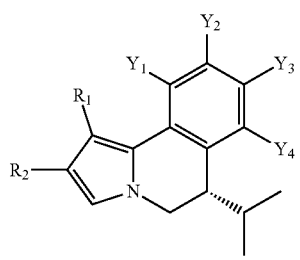

(XII-8) 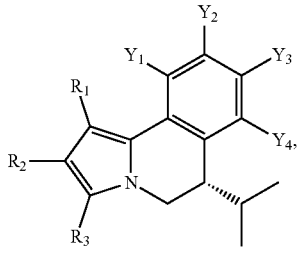
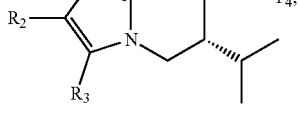

wherein $Y_1$, $Y_2$, $Y_3$, $Y_4$, $R_1$, $R_2$ and $R_3$ are as previously defined and $R_1$, $R_2$ and $R_3$ are not hydrogen. Preferably, $Y_1$ is H, F or cycloproply; $Y_2$ is —OH; $Y_3$ is —COOR$_{11}$; $Y_4$ is hydrogen; and $R_1$, $R_2$, and $R_3$ are each independently selected from optionally substituted aryl and optionally substituted heteroaryl.

In another embodiment, the compound of Formula (I) is represented by one of Formulae (XIII-1)~(XIII-6), or a pharmaceutically acceptable salt thereof:

(XIII-1) 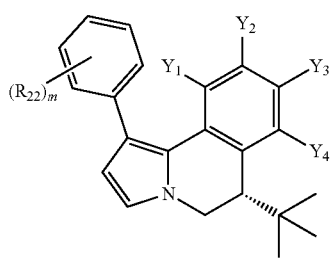

(XIII-2) 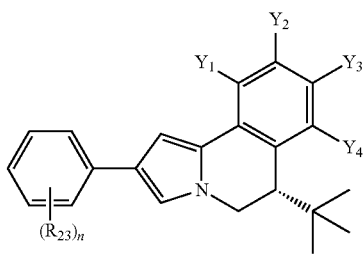

(XIII-3) 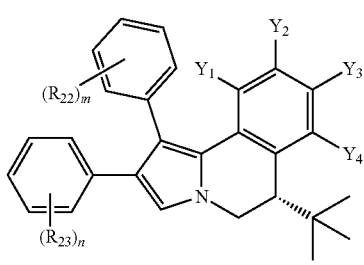

(XIII-4)

(XIII-5)

(XIII-6)

wherein $R_{22}$ and $R_{23}$ are each independently selected from halo, CN, $-OR_{11}$, $-N_{11}R_{12}$, and optionally substituted $C_1$-$C_6$ alkyl; m is 0, 1, 2, 3 or 4; n is 0, 1, 2, 3, or 4; $Y_1$, $Y_2$, $Y_3$, and $Y_4$ are as previously defined. Preferably, $Y_1$ is H, F or cycloproply; $Y_2$ is $-OH$; $Y_3$ is $-COOR_{11}$; and $Y_4$ is hydrogen.

In another embodiment, the compound of Formula (I) is represented by one of Formulae (XIV-1)~(XIV-6), or a pharmaceutically acceptable salt thereof:

(XIV-1)

(XIV-2)

(XIV-3)

(XIV-4)

(XIV-5)

(XIV-6)

wherein $Y_1$, $Y_2$, $R_{22}$, $R_{23}$, m and n are as previously defined. Preferably, $Y_1$ is H, F or cycloproply; and $Y_2$ is $-OH$.

In another embodiment, the compound of Formula (I) is represented by one of Formulae (XV-1)~(XV-6), or a pharmaceutically acceptable salt thereof:

(XV-1)

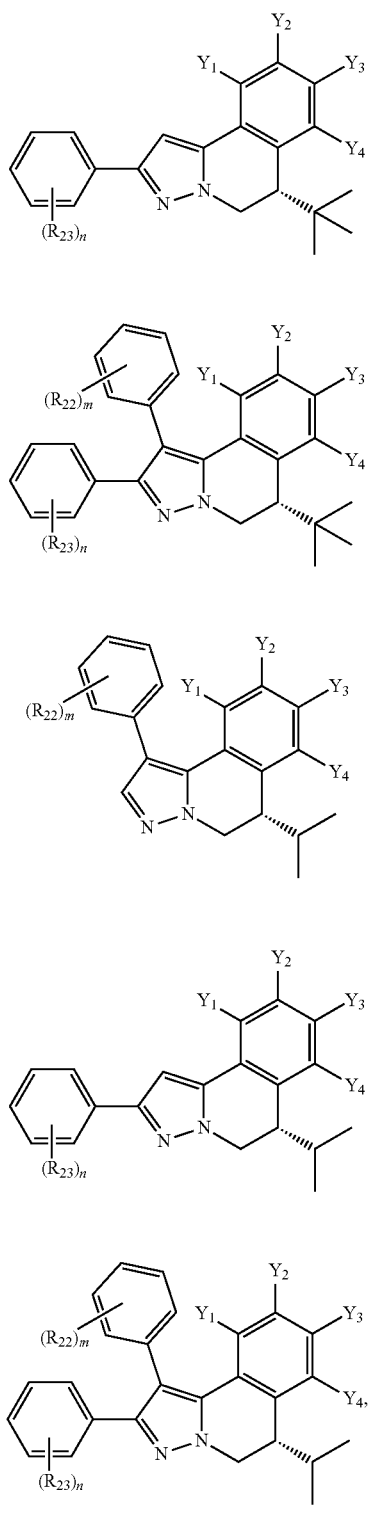

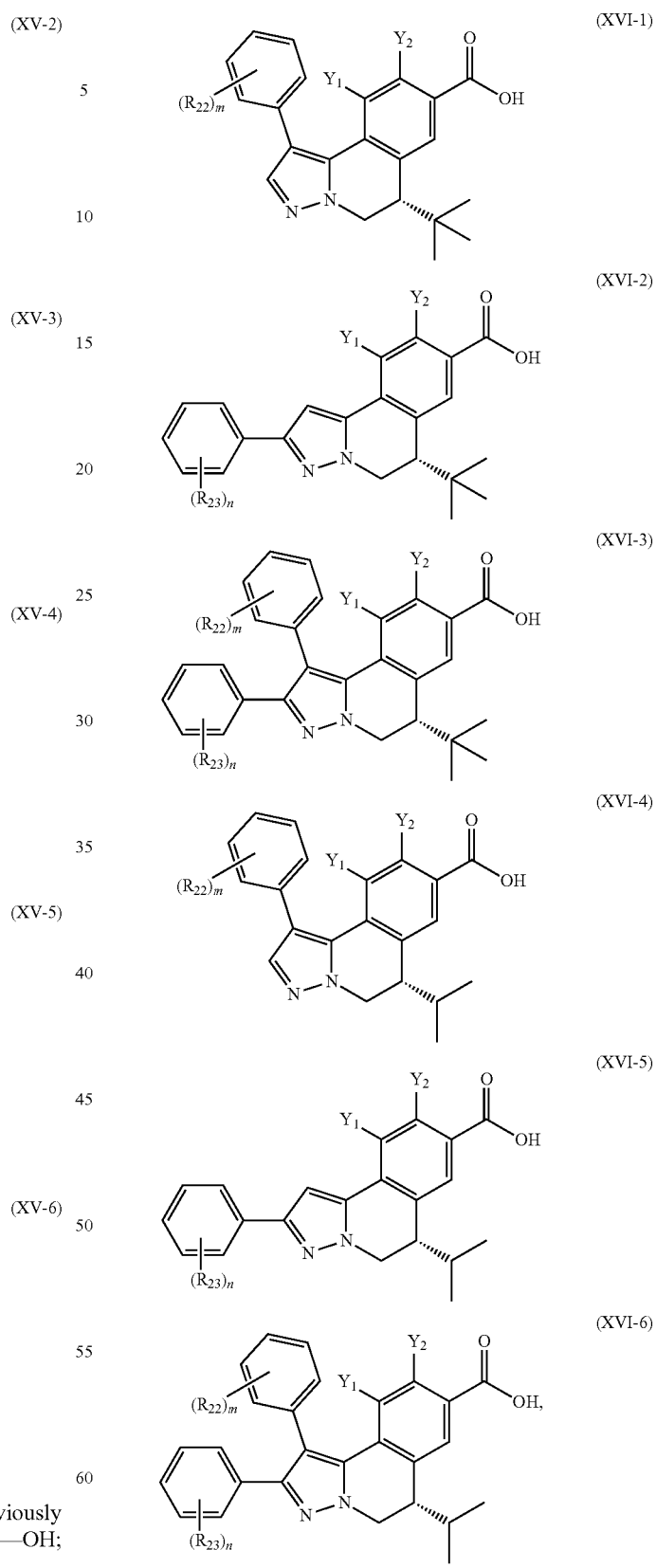

wherein $Y_1$, $Y_2$, $Y_3$, $Y_4$, $R_{22}$, $R_{23}$, m and n are as previously defined. Preferably, $Y_1$ is H, F or cycloproply; $Y_2$ is —OH; $Y_3$ is —COOR$_{11}$; and $Y_4$ is hydrogen.

In another embodiment, the compound of Formula (I) is represented by one of Formulae (XVI-1)~(XVI-6), or a pharmaceutically acceptable salt thereof:

wherein $Y_1$, $Y_2$, $R_{22}$, $R_{23}$, m and n are as previously defined. Preferably, $Y_1$ is H, F, or cycloproply; and $Y_2$ is —OH.

In another embodiment, the compound of the invention is represented by Formula (II-1)~Formula (II-8), or Formula (III-1)~Formula (III-8), or Formula (XI-1)~(XI-8), or Formula (XII-1)~Formula (XII-8), or a pharmaceutically acceptable salt thereof, wherein at least one of $R_1$, $R_2$, and $R_3$ is independently selected from the groups in Table 1. In another embodiment, the compound of the invention is represented by Formula (V-1)~Formula (V-8), or Formula (VI-1)~Formula (VI-8), or Formula (VII-1)~(VIII-8), or Formula (VII-1a)~(VIII-8a), or Formula (VIII-1)~Formula (VIII-6), or Formula (IX-1)~Formula (IX-6), or Formula (X-1)~Formula (X-6), or a pharmaceutically acceptable salt thereof, wherein at least one of $R_1$ and $R_2$ is independently selected from the groups in Table 1.

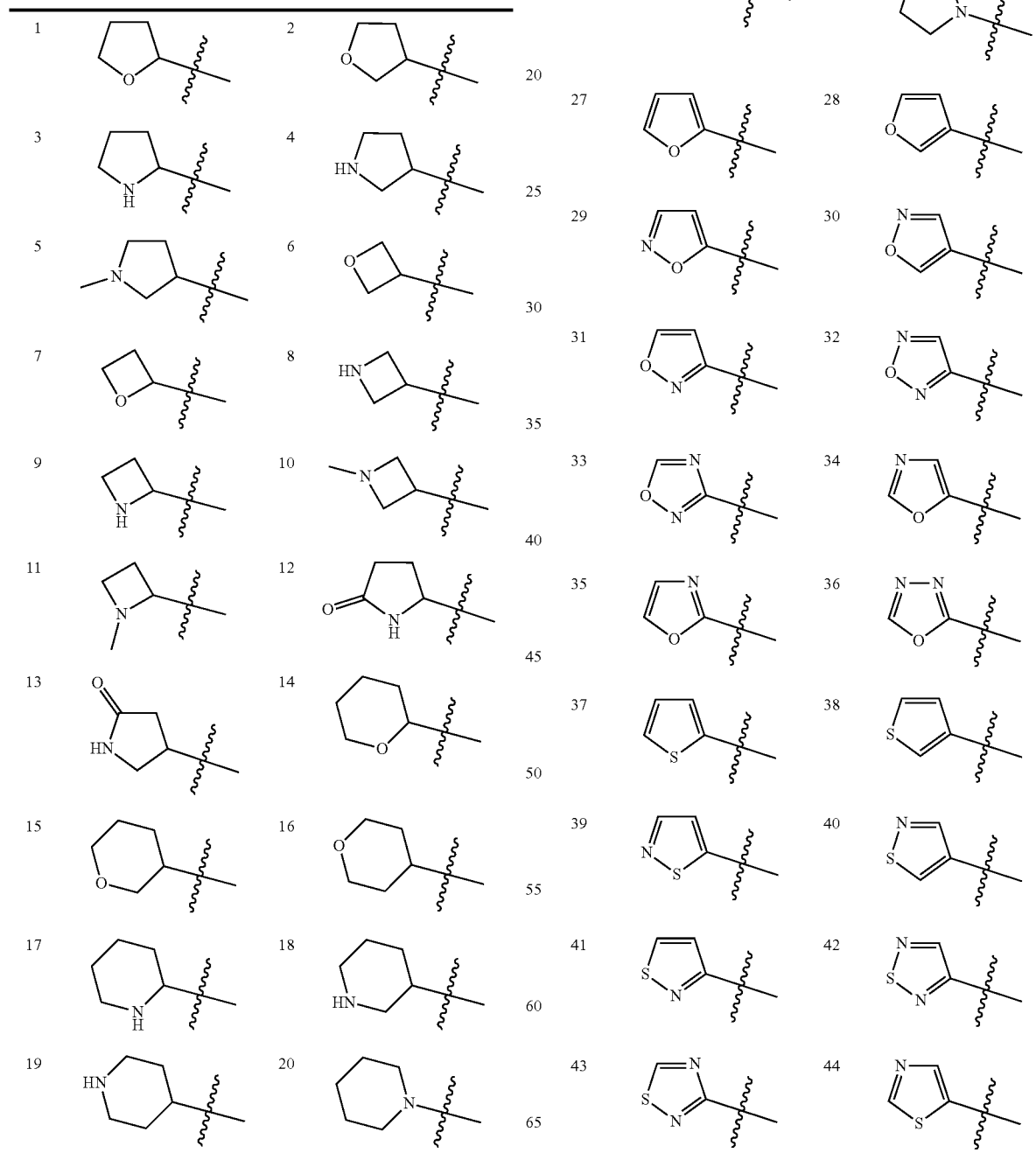

TABLE 1

TABLE 1-continued
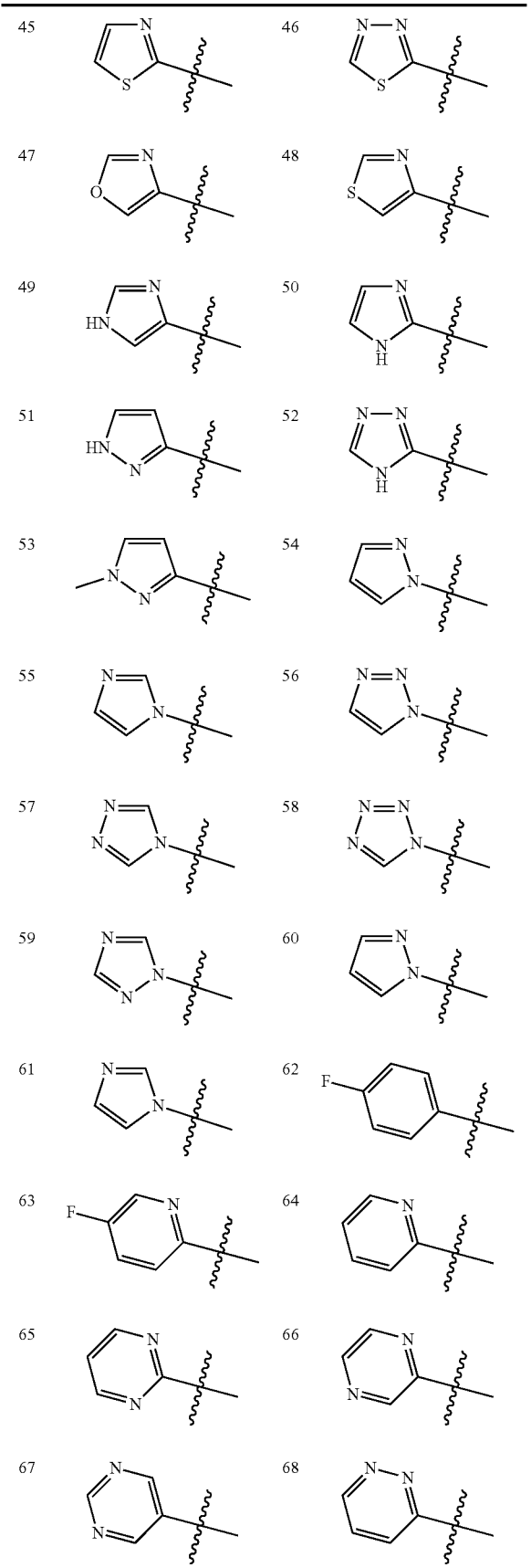
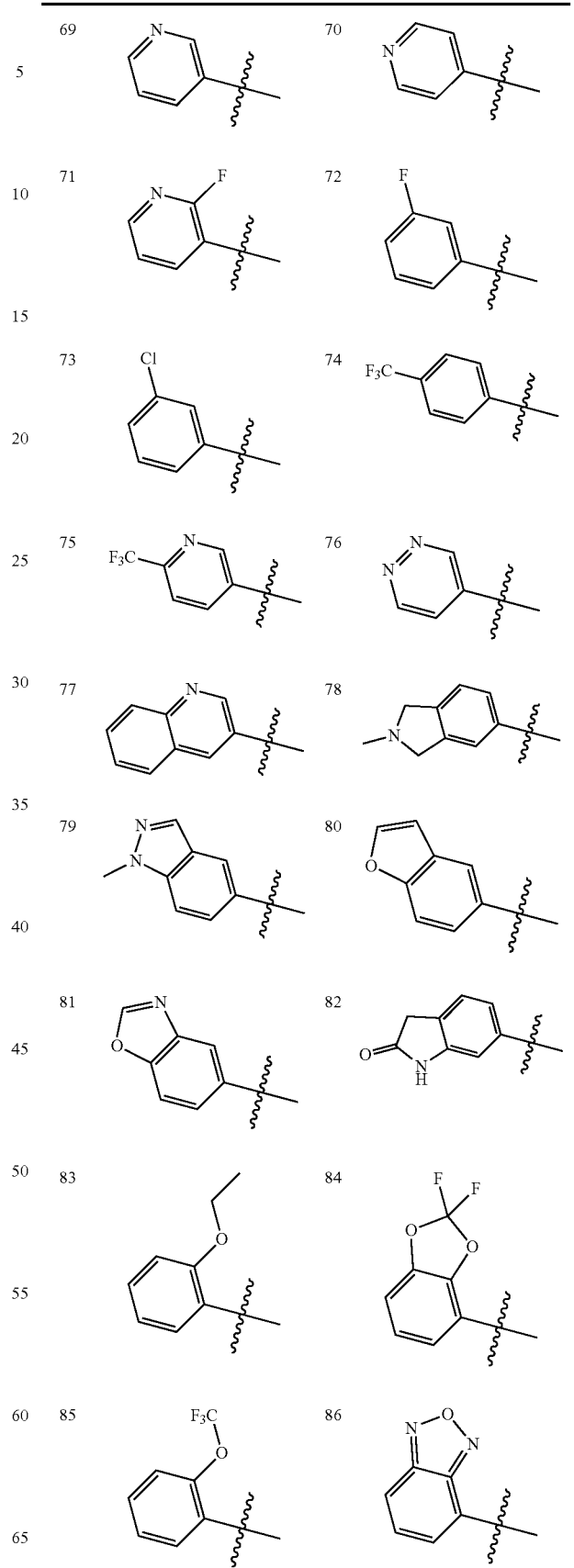

TABLE 1-continued

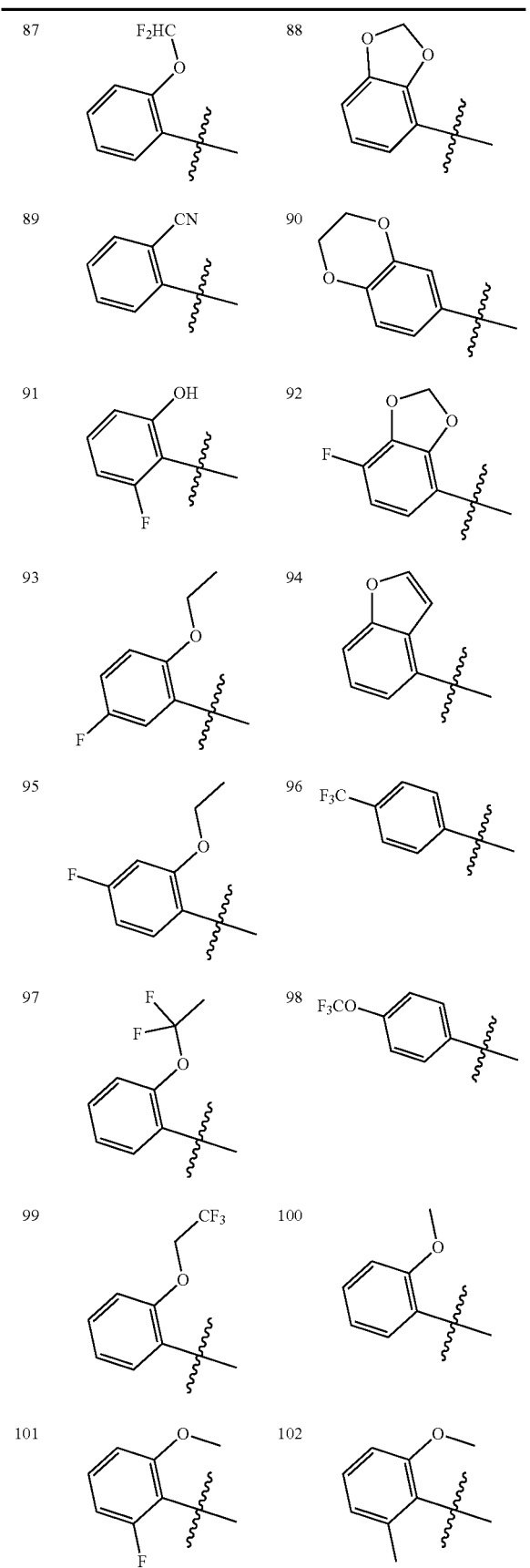

TABLE 1-continued

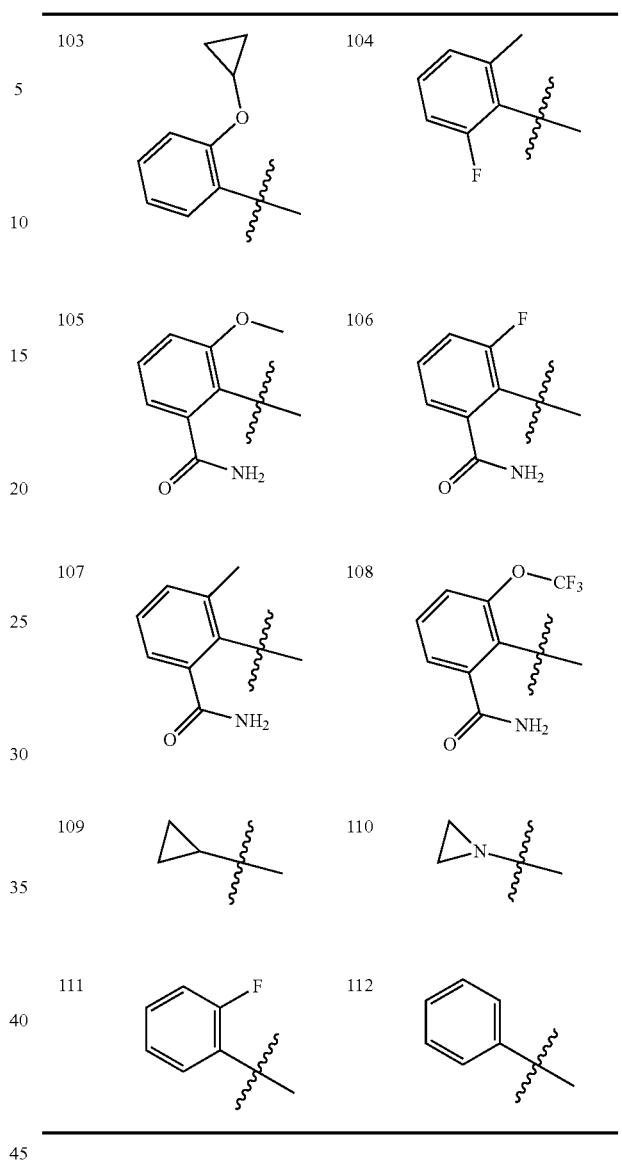

In another embodiment, the compound of Formula (I) is represented by Formula (XVII), or a pharmaceutically acceptable salt thereof:

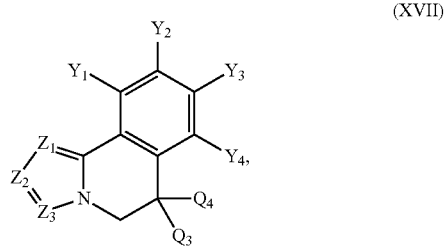

(XVII)

wherein $Y_1$, $Y_2$, $Y_3$, $Y_4$, $Z_1$, $Z_2$, $Z_3$, $Q_1$, and $Q_2$ are as previously defined.

In another embodiment, the compound of Formula (I) is represented by Formula (XVIIa) or a pharmaceutically acceptable salt thereof:

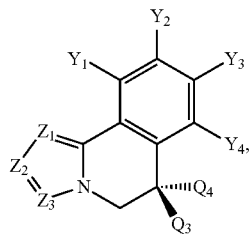

(XVIIa)

wherein $Y_1$, $Y_2$, $Y_3$, $Y_4$, $Z_1$, $Z_2$, $Z_3$, $Q_1$, and $Q_2$ are as previously defined. Preferably, $Q_3$ is hydrogen or optionally substituted $C_1$-$C_6$ alkyl; and $Q_4$ is hydrogen, optionally substituted $C_1$-$C_6$ alkyl, optionally substituted —$C_1$-$C_6$ alkoxy, optionally substituted —$C_3$-$C_8$ cycloalkyl; optionally substituted —$C_3$-$C_5$ cycloalkenyl; optionally substituted 3- to 8-membered heterocycloalkyl. More preferably, $Q_3$ is optionally substituted $C_1$-$C_6$ alkyl or hydrogen; $Q_4$ is optionally substituted $C_1$-$C_6$ alkyl or hydrogen.

In another embodiment, the compound of Formula (I) is represented by Formula (XVIIa) or a pharmaceutically acceptable salt thereof, wherein $Y_1$, $Y_2$, $Y_3$, $Y_4$, $Z_1$, $Z_2$, and $Z_3$ are as previously defined, $Q_3$ is optionally substituted methyl and $Q_4$ is optionally substituted methyl.

In another embodiment, the compound of Formula (I) is represented by one of Formulae (XVIII-1)~(XVIII-6), or a pharmaceutically acceptable salt thereof:

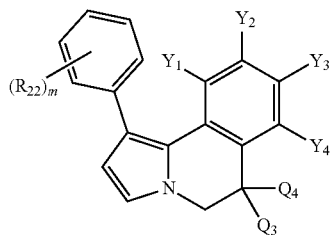

(XVIII-1)

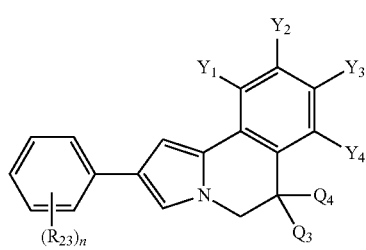

(XVIII-2)

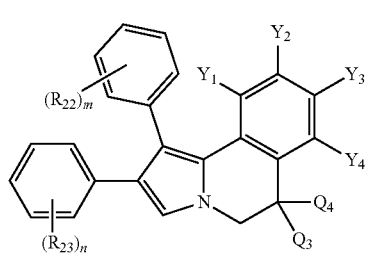

(XVIII-3)

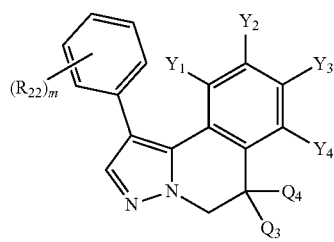

(XVIII-4)

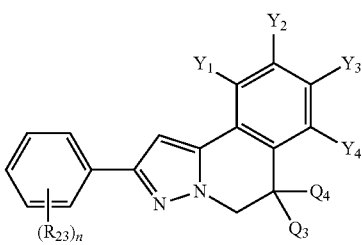

(XVIII-5)

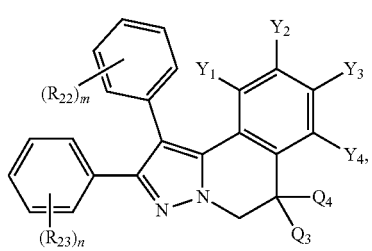

(XVIII-6)

wherein $Y_1$, $Y_2$, $Y_3$, $Y_4$, $Q_3$, $Q_4$, $R_{22}$, $R_{23}$, m and n are as previously defined. Preferably, $Q_3$ is hydrogen or optionally substituted $C_1$-$C_6$ alkyl; and $Q_4$ is hydrogen, optionally substituted $C_1$-$C_6$ alkyl, optionally substituted —$C_1$-$C_6$ alkoxy, optionally substituted —$C_3$-$C_8$ cycloalkyl; optionally substituted —$C_3$-$C_8$ cycloalkenyl, or optionally substituted 3- to 8-membered heterocycloalkyl.

In another embodiment, the compound of Formula (I) is represented by one of Formulae (XIX-1)~(XIX-6), or a pharmaceutically acceptable salt thereof:

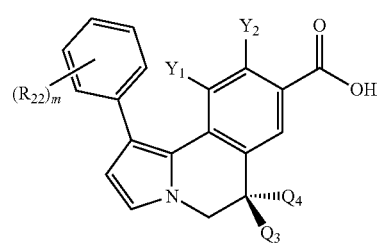

(XIX-1)

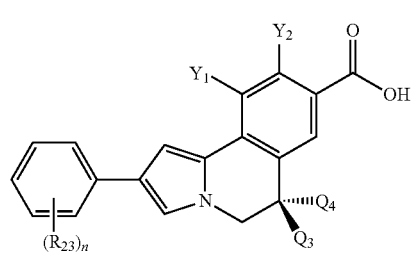

(XIX-2)

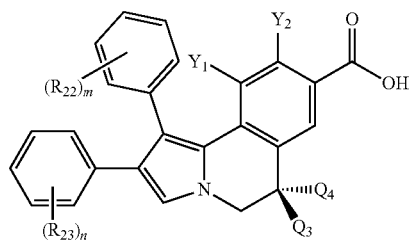
(XIX-3)

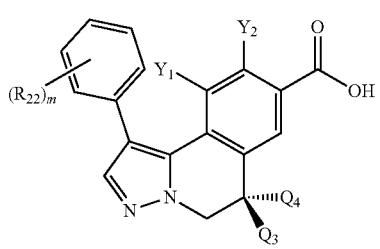
(XIX-4)

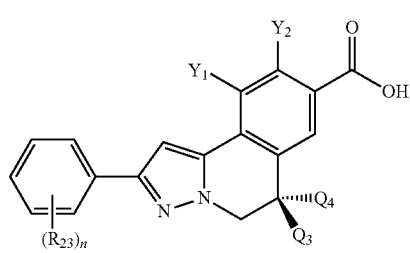
(XIX-5)

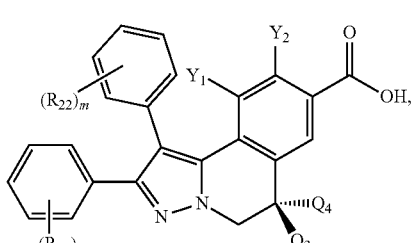
(XIX-6)

wherein $Y_1$, $Y_2$, $Q_3$, $Q_4$, $R_{22}$, $R_{23}$, m and n are as previously defined.

In another embodiment, the compound of Formula (I) is represented by one of Formulae (XX-1)~(XX-6), or a pharmaceutically acceptable salt thereof:

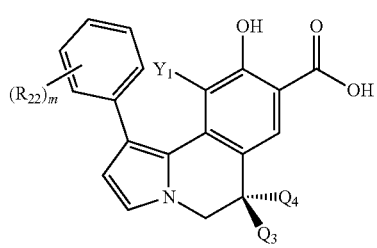
(XX-1)

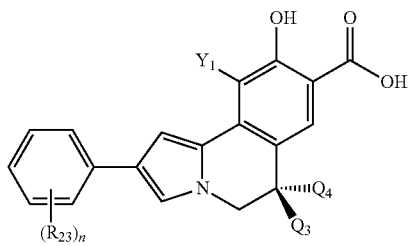
(XX-2)

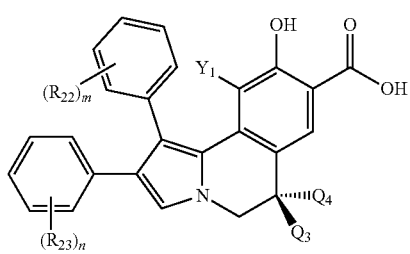
(XX-3)

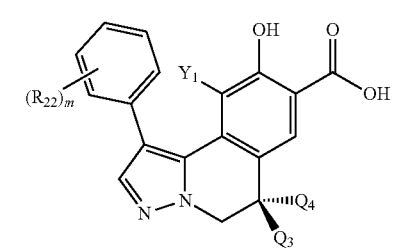
(XX-4)

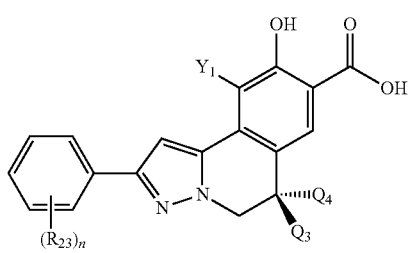
(XX-5)

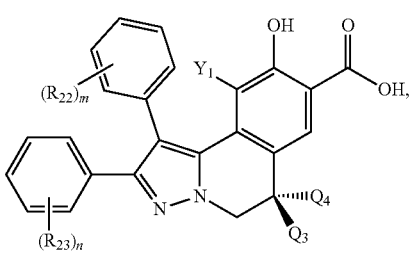
(XX-6)

wherein $Y_1$, $Q_3$, $Q_4$, $R_{22}$, $R_{23}$, m and n are as previously defined.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from core inhibitor, which includes GLS4, GLS4JHS, JNJ-379, ABI-H0731, ABI-H2158, AB-423, AB-506, WX-066, and QL-0A6A; immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or STING (stimulator of interferon genes) modulator; or TLR modulators such as TLR-7 agonists, TLR-8 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein, or RNA interference (RNAi) or small interfering RNA (siRNA) such as ARC-520, ARC-521, ARB-1467, and ALN-HBV RNAi, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139, RG7834, and AB-452. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (12-benzyl-8-hydroxy-2-(2-methoxy-ethoxy)adenine), AZD 8848 (methyl [3-({[3-(6-amino-2-butoxy-8-oxo-7,8-dihydro-9H-purin-12-yl)propyl][3-(4-morpholinyl)propyl] amino Imethyl)phenyl] acetate), GS-9620 (4-Amino-2-butoxy-8-[3-(2-pyrrolidinylmethyl)benzyl]-7,8-dihydro-6(5H)-pteridinone), AL-034 (TQ-A3334), and RO6864018.

In another embodiment of the combination therapy, the TLR-8 agonist is GS-9688.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_5$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O—heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —$CO_2$—$C_2$-$C_5$ alkenyl, —$CO_2$—$C_2$-$C_8$ alkynyl, $CO_2$—$C_3$-$C_{12}$-cycloalkyl, —$CO_2$— aryl, $CO_2$-heteroaryl, $CO_2$— heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH— heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)— heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$— $C_2$-$C_8$-alkynyl, —$SO_2NH$—$C_3$-$C_{12}$-cycloalkyl, —$SO_2NH$-aryl, —$SO_2NH$-heteroaryl, —$SO_2NH$— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heterocycloalkyl, -heterocycloalkyl, —$C_3$-$C_{12}$-cycloalkyl, polyalkoxyalkyl, polyalkoxy, -methoxymethoxy, -methoxyethoxy, —SH, —S—$C_2$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably $C_1$ and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —$C_1$, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts,

*Protective Groups in Organic Synthesis,* 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Combination and Alternation Therapy

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

ABBREVIATIONS

Abbreviations which may be used in the descriptions of the scheme and the examples that follow are: Ac for acetyl;

AcOH for acetic acid; Boc₂O for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or (i-Pr)₂EtN for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; Et₂O for diethyl ether; HATU for O-(7-azabenzotriazol-2-yl)-N,N,N',N',-tetramethyluronium Hexafluorophosphate; HCl for hydrogen chloride; $K_2CO_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethylpiperidinate; MeOH for methanol; Mg for magnesium; MOM for methoxymethyl; Ms for mesyl or —SO₂—CH₃; NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4Cl$ for ammonium chloride; Ni for nickel; OH for hydroxyl; $OsO_4$ for osmium tetroxide; OTf for triflate; PPA for polyphophoric acid; PTSA for p-toluenesulfonic acid; PPTS for pyridinium p-toluenesulfonate; TBAF for tetrabutylammonium fluoride; TEA or Et₃N for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or PPh₃ for triphenyl-phosphine; Tos or Ts for tosyl or —SO₂—C₆H₄CH₃; Ts₂O for tolylsulfonic anhydride or tosyl-anhydride; TsOH for p-tolylsulfonic acid; Pd for palladium; Ph for phenyl; Pd₂(dba)₃ for tris(diben-zylideneacetone) dipalladium (0); Pd(PPh₃)₄ for tetrakis(triphenylphosphine)-palladium (0); PdCl₂(PPh₃)₂ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

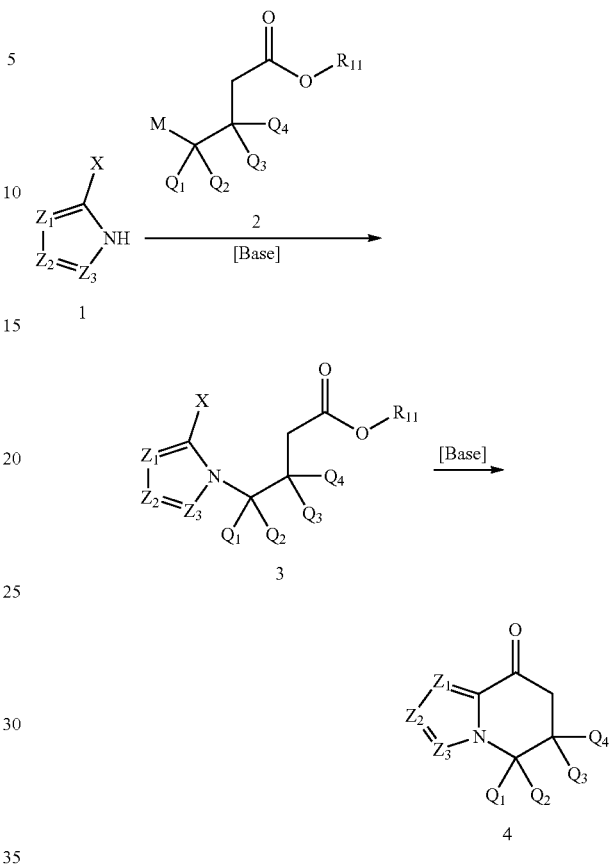

Illustrated in Scheme 1, compounds such as 4 ($Z_1$, $Z_2$, $Z_3$, $Q_1$, $Q_2$, $Q_3$, and $Q_4$ as defined previously) can be prepared according to the illustrated synthetic methods herein, or by similar methods known to those skilled in the art. Intermediate 1 can be reacted in a carbon-nitrogen bond forming reaction with ester 2 (M defined as halogen, OMs, OAc, OTf, OTs, or ONs; Ru as defined previously), typically mediated by a base (denoted as [Base]) including, but not limited to: $K_2CO_3$, $Cs_2CO_3$, KOAc, NaOtBu, NaOH, KOH, NaH, Et₃N, or DBU. Intermediate 3 can be reacted in a ring-closing step, typically mediated by a base (denoted as [Base]) including, but not limited to: nBuLi or sBuLi, to produce ketone 4.

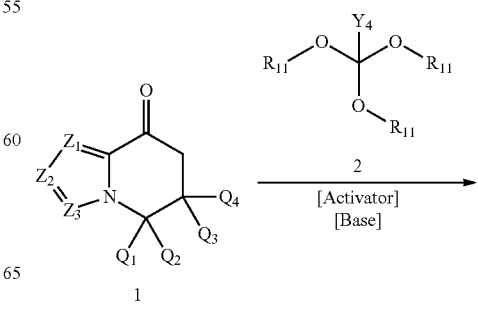

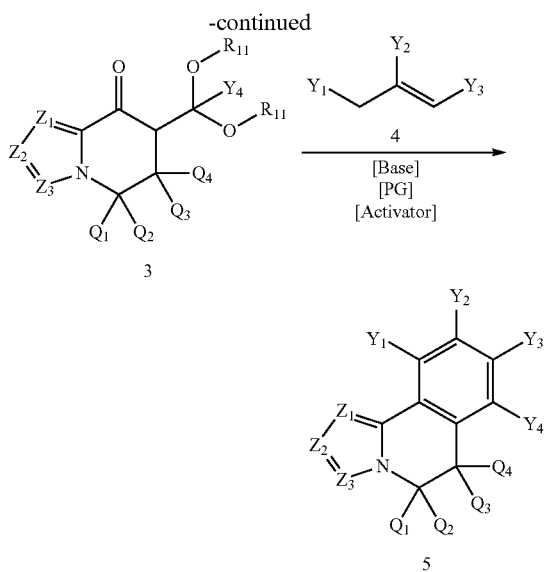

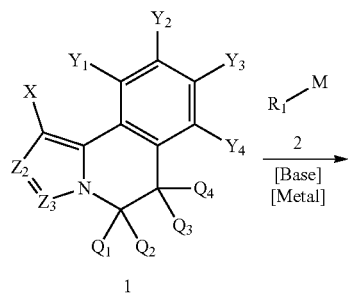

Illustrated in Scheme 2, compounds such as 5 ($Z_1$, $Z_2$, $Z_3$, $Q_1$, $Q_2$, $Q_3$, $Q_4$, $Y_1$, $Y_2$, $Y_3$, and $Y_4$ as defined previously) can be prepared according to the illustrated synthetic methods herein, or by similar methods known to those skilled in the art. Ketone 1 can be reacted in a homologation reaction with orthoester 2 ($R_{11}$ as defined previously), typically mediated by a base (denoted as [Base]) including, but not limited to: $K_2CO_3$, $Cs_2CO_3$, DIPEA, $Et_3N$, or DBU and an activator (denoted as [Activator]) including, but not limited to: $BF_3 \cdot OEt_2$, $Ti(OiPr)_4$, or $B(C_6F_5)_3$. Intermediate 3 can be reacted in an annulation reaction with alkene 4, which is first deprotonated using a base (denoted as [Base]) including, but not limited to: LiHMDS, LDA, or LiTMP, then protected using an electrophilic reagent (denoted as [PG]) including, but not limited to: TMSCl, TMSOTf, or TESOTf, then reacted with an activator (denoted as [Activator]) including, but not limited to: $TiCl_4$ or $BF_3 \cdot OEt_2$, to produce compound 5.

Scheme 3:

Illustrated in Scheme 3, compounds such as 3 ($Z_2$, $Z_3$, $R_1$, $Q_1$, $Q_2$, $Q_3$, $Q_4$, $Y_1$, $Y_2$, $Y_3$, and $Y_4$ as defined previously) can be prepared according to the illustrated synthetic methods herein, or by similar methods known to those skilled in the art. Compound 1 (X defined as halogen, —B(OH)$_2$, —BF$_3$K, —B(pin), —OTf, or —OMs) can be reacted in a coupling reaction with 2 (M defined as halogen, —B(OH)$_2$, —BF$_3$K, —B(pin), —OTf, or —OMs) that is mediated by a metal-containing reagent (denoted as [Metal]) including, but not limited to reagents that contain: Pd, Cu, Zn, Fe, Ir, Ru, Rh, or Ni, and a base (denoted as [Base]) including, but not limited to: KOAc, $K_2CO_3$, $Cs_2CO_3$, $Et_3N$, or $K_3PO_4$ to produce 3.

Scheme 4:

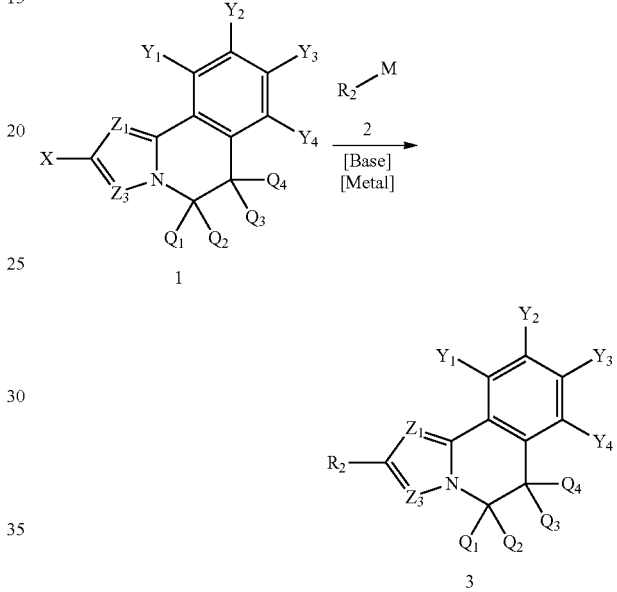

Illustrated in Scheme 4, compounds such as 3 ($Z_1$, $Z_3$, $R_2$, $Q_1$, $Q_2$, $Q_3$, $Q_4$, $Y_1$, $Y_2$, $Y_3$, and $Y_4$ as defined previously) can be prepared according to the illustrated synthetic methods herein, or by similar methods known to those skilled in the art. Compound 1 (X defined as halogen, —B(OH)$_2$, —BF$_3$K, —B(pin), —OTf, or —OMs) can be reacted in a coupling reaction with 2 (M defined as halogen, —B(OH)$_2$, —BF$_3$K, —B(pin), —OTf, or —OMs) that is mediated by a metal-containing reagent (denoted as [Metal]) including, but not limited to reagents that contain: Pd, Cu, Zn, Fe, Ir, Ru, Rh, or Ni, and a base (denoted as [Base]) including, but not limited to: KOAc, $K_2CO_3$, $Cs_2CO_3$, $Et_3N$, or $K_3PO_4$ to produce 3.

Scheme 5:

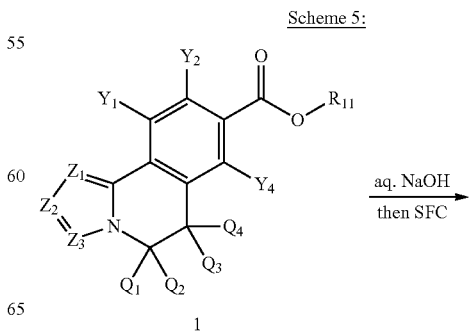

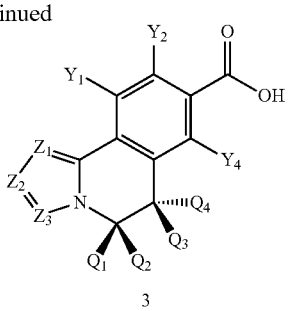

Illustrated in Scheme 5, compounds such as 2 ($Z_1$, $Z_2$, $Z_3$, $Q_1$, $Q_2$, $Q_3$, $Q_4$, $Y_1$, $Y_2$, and $Y_4$ as defined previously) can be prepared according to the illustrated synthetic methods herein, or by similar methods known to those skilled in the art. Intermediate 1 ($R_{11}$ as defined previously) can be reacted under hydrolytic conditions mediated by NaOH, and followed by purification using SFC, compounds such as 2 can be obtained with high optical purity.

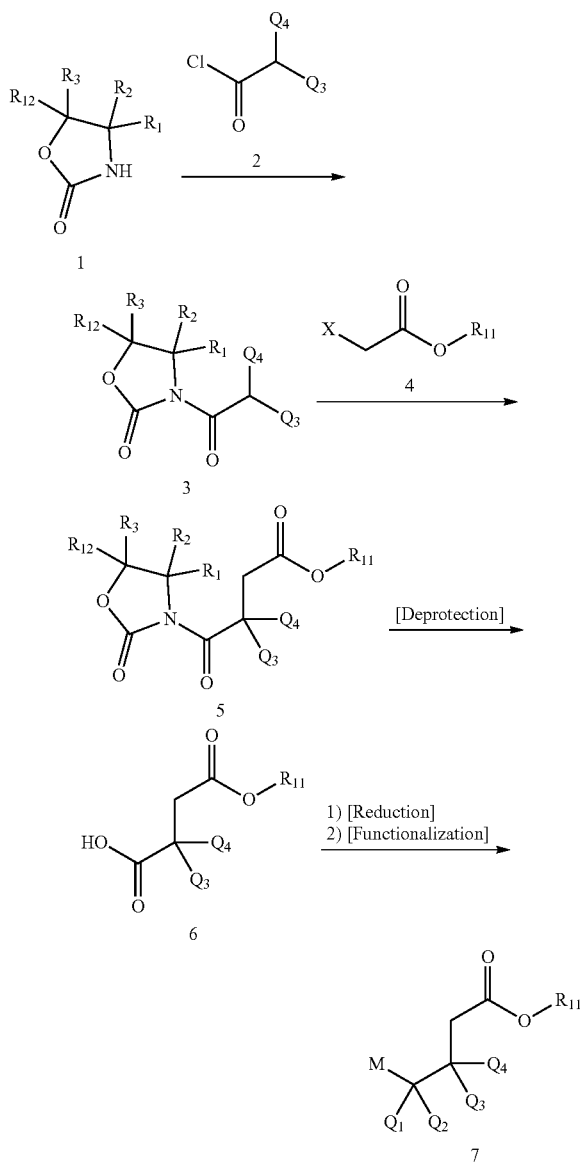

Illustrated in Scheme 6, compounds such as 7 ($Q_1$, $Q_2$, $Q_3$, $Q_4$, and $R_{11}$ as defined previously; M defined as halogen, OMs, OAc, OTf, OTs, or ONs) can be prepared according to the illustrated synthetic methods herein, or by similar methods known to those skilled in the art. Carbamate 1 ($R_{12}$ as defined previously) can be reacted with acid chloride 2 to produce intermediate 3. This can undergo an alkylation reaction with ester 4 (X defined as halogen, —OTf, —OTs, or —OMs) and a base including, but not limited to: LDA, LiHMDS, or NaH, to produce intermediate 5. This can undergo a deprotection reaction (denoted as [Deprotection]) to produce acid 6. Following net reduction (denoted as [Reduction]) and functionalization (denoted a [Functionalization]), compound 7 is produced.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. [M+H]$^+$ refers to mono-isotopic molecular weights.

NMR spectra were run on a Bruker 400 MHz spectrometer. Spectra were measured at 298K and referenced using the solvent peak. Chemical shifts for $^1$H NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Ex1: Synthesis of (S)-6-(tert-butyl)-2-(4-fluorophenyl)-9-hydroxy-5,6-dihydropyrazolo[5,1-a]isoquinoline-8-carboxylic acid

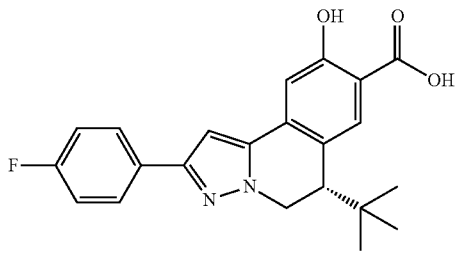 [SMILES: CC(C)(C)[C@@H]1Cn2nc(-c3ccc(F)cc3)cc2-c2cc(O)c(C(=O)O)cc21]

Step 1: Into a 10-L 4-necked round-bottom flask purged and maintained with an inert atmosphere of nitrogen, was placed THE (4500.00 mL), LiCl (171.00 g, 4033.590 mmol, 1.59 equiv), TEA (641.00 g, 6334.61 mmol, 2.49 equiv). This was followed by the addition of 2,2-dimethylpropanoyl chloride (357.00 g, 2960.69 mmol, 1.17 equiv) dropwise with stirring at 0° C. in 10 min. To this was added a solution of 3,3-dimethylbutanoic acid (354.00 g, 3047.521 mmol, 1.20 equiv) in THE (1500 mL) dropwise with stirring at 0° C. in 30 min. To the mixture was added (4R)-4-benzyl-1,3-oxazolidin-2-one (450.00 g, 2539.46 mmol, 1.00 equiv), DMAP (15.51 g, 126.97 mmol, 0.05 equiv) at 0° C. The resulting solution was stirred for 1 overnight at room temperature. The reaction was then quenched by the addition of 5 L of water. The resulting solution was extracted with 2×3 L of ethyl acetate. The combined organic phase was washed with 1×3 L of saturated aqueous NaHCO₃. The resulting mixture was washed with 1×3 L of brine. The mixture was dried over anhydrous sodium sulfate and concentrated under vacuum. The crude product was purified by re-crystallization from ether. This resulted in 590 g (84.38%) of (4R)-4-benzyl-3-(3,3-dimethylbutanoyl)-1,3-oxazolidin-2-one as a white solid.

Step 2: Into a 20-L 4-necked round-bottom flask purged and maintained with an inert atmosphere of nitrogen, was placed THE (5900.00 mL), diisopropylamine (345.80 g, 3423.76 mmol, 1.60 equiv). This was followed by the addition of n-BuLi (1284.00 mL, 3214.11 mmol, 2.50 equiv, 2.5 M) drop wise with stirring at −20° C. in 30 min. The resulting solution was stirred for 30 min at −20° C. To this was added a solution of (4R)-4-benzyl-3-(3,3-dimethylbutanoyl)-1,3-oxazolidin-2-one (590.00 g, 2142.74 mmol, 1.00 equiv) in THE (2000 mL) dropwise with stirring at −78° C. in 30 min. The resulting solution was stirred at −40° C. for 2.5 h. To the mixture was added tert-butyl 2-bromoacetate (832.00 g, 4265.44 mmol, 1.99 equiv) drop wise with stirring at −78° C. in 20 min. The resulting mixture was warmed to room temperature slowly. The resulting solution was stirred for 30 min at room temperature. The reaction was then quenched by the addition of 200 g of AcOH at 0° C. The resulting solution was diluted with 5 L of H₂O. The resulting solution was extracted with 2×5 L of ethyl acetate. The combined organic phase was washed with 2×5 L of brine. The mixture was dried over anhydrous sodium sulfate and concentrated under vacuum. The residue was applied onto a silica gel column with ethyl acetate/petroleum ether (1:10). This resulted in 335 g (40.14%) of tert-butyl (3R)-3-[(4R)-4-benzyl-2-oxo-1,3-oxazolidine-3-carbonyl]-4,4-dimethylpentanoate as a white solid.

Step 3: Into a 20-L 4-necked round-bottom flask purged and maintained with an inert atmosphere of nitrogen, was placed THE (7290.00 mL), H₂O (2430.00 mL), H₂O₂ (314.60 g, 2772.84 mmol, 8.00 equiv, 30%), LiOH (33.20 g, 1386.42 mmol, 4.00 equiv), tert-butyl (3R)-3-[(4R)-4-benzyl-2-oxo-1,3-oxazolidine-3-carbonyl]-4,4-dimethylpentanoate (135.00 g, 346.605 mmol, 1.00 equiv). The resulting solution was stirred for 3 days at 30° C. The reaction was then quenched by the addition of 2776 mL of Na₂SO₃ (1N). The resulting solution was extracted with 2×5 L of ethyl acetate. The combined organic phase was washed with 2×5 L of brine. The mixture was dried over anhydrous sodium sulfate and concentrated under vacuum. The residue was applied onto a silica gel column with ethyl acetate/petroleum ether (1:5). The crude product (32 g) was purified by silica gel chromatography to produce 22.9 g (28.69%) of (2R)-2-[2-(tert-butoxy)-2-oxoethyl]-3,3-dimethylbutanoic acid as a light yellow semi-solid. ESI MS m/z=229.1 [M−H]⁻. H-NMR (400 MHz, CDCl₃, ppm): δ 2.747-2.592 (2H, m), 2.463-2.406 (1H, m), 1.449 (9H, s), 1.020 (9H, s).

Step 4: Into a 2-L 4-necked round-bottom flask purged and maintained with an inert atmosphere of nitrogen, was placed (2R)-2-[2-(tert-butoxy)-2-oxoethyl]-3,3-dimethylbutanoic acid (52.00 g, 225.78 mmol, 1.00 equiv). This was followed by the addition of THF (500.00 mL). To this was added BH₃-Me₂S (45.16 mL, 2.00 equiv, 10 M) drop wise with stirring at 0-10° C. in 20 min. The resulting solution was stirred for overnight at room temperature. The reaction was then quenched by the addition of 500 mL of water at −10° C. The resulting solution was extracted with 2×200 mL of ethyl acetate and the organic layers combined. The solids were filtered out. The resulting mixture was washed with 300 mL of saturated aqueous NaHCO₃. The resulting mixture was washed with 300 mL of H₂O. The mixture was dried over anhydrous sodium sulfate and concentrated under vacuum. This resulted in 45 g (92.13%) of tert-butyl (3R)-3-(hydroxymethyl)-4,4-dimethylpentanoate as colorless oil.

Step 5: Into a 1000-mL 4-necked round-bottom flask purged and maintained with an inert atmosphere of nitrogen, was placed tert-butyl (3R)-3-(hydroxymethyl)-4,4-dimethylpentanoate (45.00 g, 208.024 mmol, 1.00 equiv), DCM (450.00 mL). This was followed by the addition of TEA (42.10 g, 416.048 mmol, 2.00 equiv) drop wise with stirring at 0° C. in 10 min. To this was added MsCl (26.21 g, 228.827 mmol, 1.10 equiv) drop wise with stirring at 0° C. in 10 min. The resulting solution was stirred for 2 h at 0-10° C. The reaction was then quenched by the addition of 200 mL of water at 0° C. The resulting solution was extracted with 2×200 mL of dichloromethane and the organic layers combined. The resulting mixture was washed with 200 ml of brine. The resulting mixture was washed with 200 mL of H₂O. The mixture was dried over anhydrous sodium sulfate and concentrated under vacuum. The residue was applied onto a silica gel column with ethyl acetate/petroleum ether (1:10). The crude product was purified by re-crystallization from PE. This resulted in 25.7709 g (42.08%) of tert-butyl (3R)-3-[(methanesulfonyloxy)methyl]-4,4-dimethylpentanoate as a white solid. ESI MS m/z=317.1 [M+Na]⁺. H-NMR: (400 MHz, CDCl₃, ppm): δ 4.397-4.383 (1H, m), 4.237-4.215 (1H, m), 3.029 (3H, s), 2.421-2.406 (1H, m), 2.319-2.292 (1H, m), 2.165-2.083 (1H, m), 1.482 (9H, s), 0.979 (9H, s).

Step 6: A vial was charged with 3,5-dibromo-1H-pyrazole (1 g, 4.56 mmol), tert-butyl (3R)-3-[(methanesulfonyloxy)methyl]-4,4-dimethylpentanoate (1 g, 3.43 mmol), potassium carbonate (853 mg, 6.18 mmol), and DMSO (10 mL). The mixture was heated to 70° C. for 18 h. After cooling to rt, the mixture was diluted with water, and the product was extracted with MBTE. Combined organics were concentrated, and the residue was purified on silica gel to provide tert-butyl (R)-3-((3,5-dibromo-1H-pyrazol-1-yl)methyl)-4,4-dimethylpentanoate (997 mg, 69%) as a clear, colorless oil.

Step 7: An oven-dried flask was charged with tert-butyl (R)-3-((3,5-dibromo-1H-pyrazol-1-yl)methyl)-4,4-dimethylpentanoate (997 mg, 2.35 mmol) and toluene (30 mL) under an inert nitrogen atmosphere. After cooling to −78° C., a solution of 1.6M nBuLi in hexanes (1.4 mL, 2.2 mmol) was added slowly. The reaction mixture was allowed to reach rt, then water was added. The product was extracted with EtOAc, and concentrated. The residue was purified on silica gel to provide (R)-2-bromo-6-(tert-butyl)-6,7-dihydropyrazolo[1,5-a]pyridin-4(5H)-one (326 mg, 51%).

Step 8: An oven-dried flask under an inert nitrogen atmosphere was charged with trimethyl orthoformate (1.8 mL, 16.6 mmol) and DCM (10 mL), then cooled to −30° C. Then BF$_3$—OEt$_2$ (2.5 mL, 19.9 mmol) was added dropwise over 15 min. This mixture was allowed to warm to 0° C. over 15 min, then cooled to −78° C. Then, (R)-2-bromo-6-(tert-butyl)-6,7-dihydropyrazolo[1,5-a]pyridin-4(5H)-one (900 mg, 3.3 mmol) was added followed by DIPEA (5.8 mL, 33.2 mmol). The reaction was allowed to reach −10° C. over 90 min. Then, the reaction mixture was poured into sat. NaHCO$_3$ (250 mL). Then, DCM (150 mL) was added. The organic layer was concentrated and the residue was purified on silica gel to provide (6R)-2-bromo-6-(tert-butyl)-5-(dimethoxymethyl)-6,7-dihydropyrazolo[1,5-a]pyridin-4(5H)-one (956 mg, 83%).

Step 9: An oven-dried vial under an inert nitrogen atmosphere was charged with (6R)-2-bromo-6-(tert-butyl)-5-(dimethoxymethyl)-6,7-dihydropyrazolo[1,5-a]pyridin-4(5H)-one (150 mg, 0.4 mmol) and DCM (5 mL). After cooling to −78° C., a solution of 1M TiCl$_4$ in DCM (1.3 mL, 1.3 mmol) was added. After 5 min at this temperature, (Z)-4-methoxy-2,2,8,8-tetramethyl-6-methylene-3,7-dioxa-2,8-disilanon-4-ene (340 mg, 1.3 mmol) was added, then the reaction mixture was allowed to reach rt. After 1 h, MeOH (2 mL) was added and the reaction mixture was concentrated and the residue purified on silica gel to provide methyl (S)-2-bromo-6-(tert-butyl)-9-hydroxy-5,6-dihydropyrazolo[5,1-a]isoquinoline-8-carboxylate (120 mg, 14%). ESI MS m/z=380.1 [M+H]$^+$.

Step 10: A vial was charged with methyl (S)-2-bromo-6-(tert-butyl)-9-hydroxy-5,6-dihydropyrazolo[5,1-a]isoquinoline-8-carboxylate (35 mg, 0.09 mmol, 1 equiv.), XPhos Pd G3 (8 mg, 0.009 mmol, 0.1 equiv.), (4-fluorophenyl)boronic acid (26 mg, 0.185 mmol, 2 equiv.), cesium carbonate (90 mg, 0.28 mmol, 3 equiv.), DMF (5 mL), and water (1 mL). The reaction mixture was stirred at 110° C. for 16 h. After cooling to room temperature, the solids were filtered, the filtrate was concentrated and purified by RPHPLC to provide (S)-6-(tert-butyl)-2-(4-fluorophenyl)-9-hydroxy-5,6-dihydropyrazolo[5,1-a]isoquinoline-8-carboxylic acid (11 mg, 31%) as a white solid. ESI MS m/z=381.1 [M+H]$^+$.

Ex2: Synthesis of (S)-6-(tert-butyl)-9-hydroxy-2-phenyl-5,6-dihydropyrazolo[5,1-a]isoquinoline-8-carboxylic acid

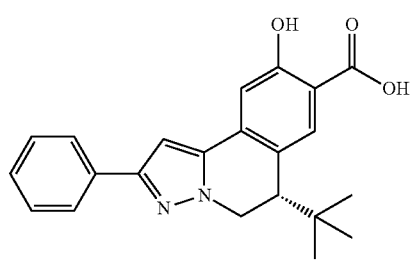 [SMILES: CC(C)(C)[C@@H]1Cn2nc(-c3ccccc3)cc2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that phenylboronic acid was used in place of (4-fluorophenyl)boronic acid in Step 10 to provide (S)-6-(tert-butyl)-9-hydroxy-2-phenyl-5,6-dihydropyrazolo[5,1-a]isoquinoline-8-carboxylic acid (5 mg). ESI MS m/z=363.1 [M+H]$^+$.

Ex3: Synthesis of (S)-6-(tert-butyl)-2-(2-fluorophenyl)-9-hydroxy-5,6-dihydropyrazolo[5,1-a]isoquinoline-8-carboxylic acid

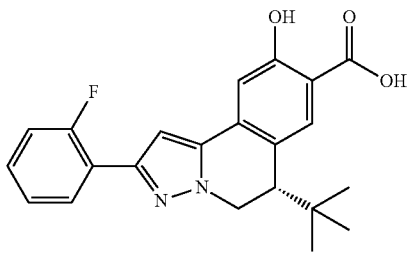 [SMILES: CC(C)(C)[C@@H]1Cn2nc(-c3ccccc3F)cc2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that (2-fluorophenyl)boronic acid was used in place of (4-fluorophenyl)boronic acid in Step 10 to provide (S)-6-(tert-butyl)-2-(2-fluorophenyl)-9-hydroxy-5,6-dihydropyrazolo[5,1-a]isoquinoline-8-carboxylic acid (4 mg). ESI MS m/z=381.1 [M+H]$^+$.

Ex4: Synthesis of (S)-6-(tert-butyl)-2-(3-fluorophenyl)-9-hydroxy-5,6-dihydropyrazolo[5,1-a]isoquinoline-8-carboxylic acid

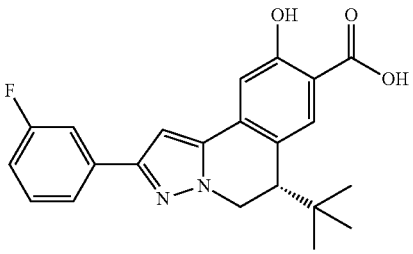 [SMILES: CC(C)(C)[C@@H]1Cn2nc(-c3cccc(F)c3)cc2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that (3-fluorophenyl)boronic acid was used in place of (4-fluorophenyl)boronic acid in Step 10 to provide (S)-6-(tert-butyl)-2-(3-fluorophenyl)-9-hydroxy-5,6-dihydropyrazolo[5,1-a]isoquinoline-8-carboxylic acid (7 mg). ESI MS m/z=381.1 [M+H]$^+$.

Ex5: Synthesis of (S)-6-(tert-butyl)-1,2-bis(3-fluorophenyl)-9-hydroxy-5,6-dihydropyrazolo[5,1-a]isoquinoline-8-carboxylic acid

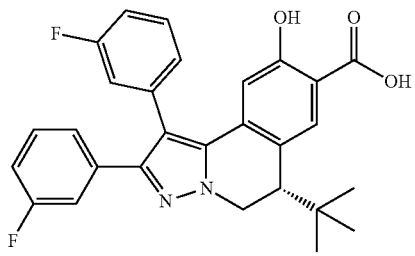 [SMILES: CC(C)(C)[C@@H]1Cn2nc(-c3cccc(F)c3)c(-c3cccc(F)c3)c2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that 3,5-dibromo-4-chloro-1H-pyrazole was used instead of 3,5-dibromo-1H-pyrazole in Step 6, and (3-fluorophenyl)boronic acid was used in place of (4-fluorophenyl)boronic acid in Step 10 to provide (S)-6-(tert-butyl)-1,2-bis(3-fluorophenyl)-9-hydroxy-5,6-dihydropyrazolo[5,1-a]isoquinoline-8-carboxylic acid (3 mg). ESI MS m/z=475.1 [M+H]$^+$.

Ex6: Synthesis of (S)-6-(tert-butyl)-1,2-bis(4-fluorophenyl)-9-hydroxy-5,6-dihydropyrazolo[5,1-a]isoquinoline-8-carboxylic acid

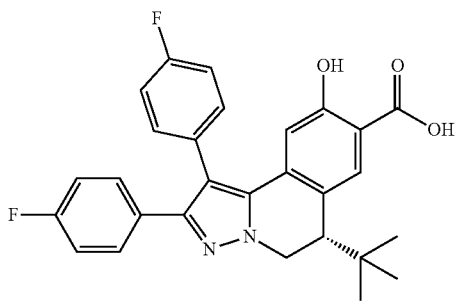 [SMILES: CC(C)(C)[C@@H]1Cn2nc(-c3ccc(F)cc3)c(-c3ccc(F)cc3)c2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that 3,5-dibromo-4-chloro-1H-pyrazole was used instead of 3,5-dibromo-1H-pyrazole in Step 6 to provide (S)-6-(tert-butyl)-1,2-bis(4-fluorophenyl)-9-hydroxy-5,6-dihydropyrazolo[5,1-a]isoquinoline-8-carboxylic acid (2 mg). ESI MS m/z=475.1 [M+H]$^+$.

Ex7: Synthesis of (S)-6-(tert-butyl)-1,2-bis(2-fluorophenyl)-9-hydroxy-5,6-dihydropyrazolo[5,1-a]isoquinoline-8-carboxylic acid

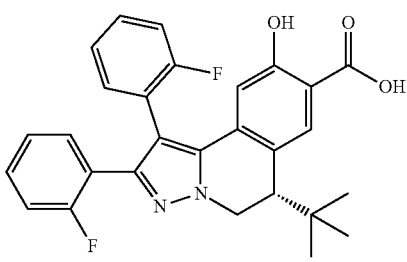 [SMILES: CC(C)(C)[C@@H]1Cn2nc(-c3ccccc3F)c(-c3ccccc3F)c2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that 3,5-dibromo-4-chloro-1H-pyrazole was used instead of 3,5-dibromo-1H-pyrazole in Step 6, and (2-fluorophenyl)boronic acid was used in place of (4-fluorophenyl)boronic acid in Step 10 to provide (S)-6-(tert-butyl)-1,2-bis(2-fluorophenyl)-9-hydroxy-5,6-dihydropyrazolo[5,1-a]isoquinoline-8-carboxylic acid (4 mg). ESI MS m/z=475.1 [M+H]$^+$.

Ex8: Synthesis of (S)-6-(tert-butyl)-9-hydroxy-1,2-diphenyl-5,6-dihydropyrazolo[5,1-a]isoquinoline-8-carboxylic acid

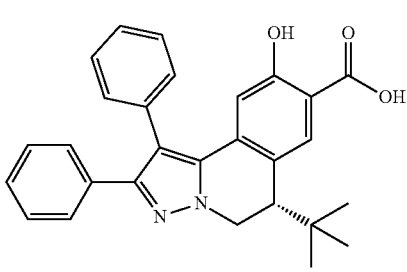 [SMILES: CC(C)(C)[C@@H]1Cn2nc(-c3ccccc3)c(-c3ccccc3)c2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that 3,5-dibromo-4-chloro-1H-pyrazole was used instead of 3,5-dibromo-1H-pyrazole in Step 6, and phenylboronic acid was used in place of (4-fluorophenyl)boronic acid in Step 10 to provide (S)-6-(tert-butyl)-9-hydroxy-1,2-diphenyl-5,6-dihydropyrazolo[5,1-a]isoquinoline-8-carboxylic acid (5 mg). ESI MS m/z=439.1 [M+H]$^+$.

Ex9: Synthesis of (S)-6-(tert-butyl)-1,2-di(furan-3-yl)-9-hydroxy-5,6-dihydropyrazolo[5,1-a]isoquinoline-8-carboxylic acid

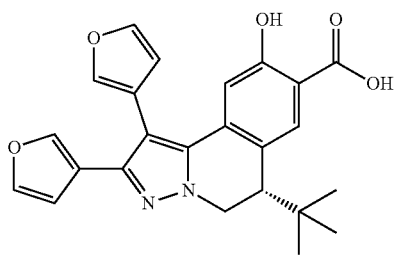 [SMILES: CC(C)(C)[C@@H]1Cn2nc(-c3ccoc3)c(-c3ccoc3)c2-c2cc(O)c(C(=O)O)cc21]

The procedure for the synthesis of the title molecule was the same as for the synthesis of (S)-6-(tert-butyl)-2-(4-fluorophenyl)-9-hydroxy-5,6-dihydropyrazolo[5,1-a]isoquinoline-8-carboxylic acid (Example 1), except that 3,5-dibromo-4-chloro-1H-pyrazole was used instead of 3,5-dibromo-1H-pyrazole in Step 6, and furan-3-boronic acid was used in place of (4-fluorophenyl)boronic acid in Step 10 to provide (S)-6-(tert-butyl)-1,2-di(furan-3-yl)-9-hydroxy-5,6-dihydropyrazolo[5,1-a]isoquinoline-8-carboxylic acid (6 mg). ESI MS m/z=419.1 [M+H]$^+$.

Biological Activity

Methods:

2.2.15 cells are passaged upon attaining confluency in DMEM/F12 media in the presence of 10% FBS, Penn/Strep, and 250 ug/mL G418. Novel compounds are 5 fold serially diluted in DMSO and added to 96 well plates containing 35,000 cells/well at a 1:200 dilution so that the final concentration of DMSO is 0.5%. On day 5, post treatment cell lysates and supernatants are harvested for analysis.

Cells are lysed using Agilent Sidestep Lysis buffer, diluted 1:100 and quantified via quantitative real time PCR. Commercially available ELISA kits are used to quantitate the viral proteins HBsAg (Alpco) or HBeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 µM; B 0.2-1 µM; C>1 µM.

Additionally, compound induced cellular toxicity is evaluated by exposing HepG2 cells seeded at 5,000 cells/well to serially diluted compound with a final DMSO concentration of 0.5% for three days. At day 3, post seeding cells are treated with ATPlite 1Step according to the manufacturer's instructions. Compound concentrations that reduce total ATP levels in wells by 50% relative to no drug controls ($CC_{50}$) are reported; $CC_{50}$ ranges are as follows: A>25 µM; B 10-25 µM; C<10 µM.

TABLE 3

Summary of Activities

| Example Number | 2.2.15 cells $EC_{50}$ (µM) | HepG2 cells $CC_{50}$ (µM) |
|---|---|---|
| 1 | C | — |
| 2 | C | — |
| 3 | C | — |
| 4 | C | — |
| 5 | C | — |
| 6 | A | A |
| 7 | A | A |
| 8 | A | A |
| 9 | C | — |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

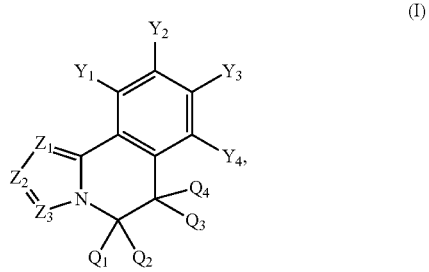

or a pharmaceutically acceptable salt, N-oxide, ester or prodrug thereof, wherein:

$Q_1$, $Q_2$, $Q_3$, and $Q_4$ are each independently selected from hydrogen, halo, —$NR_{11}R_{12}$, optionally substituted —$C_1$-$C_6$ alkyl, optionally substituted —$C_2$-$C_6$ alkenyl, optionally substituted —$C_1$-$C_6$ alkoxy, optionally substituted —$C_3$-$C_8$ cycloalkyl; optionally substituted —$C_3$-$C_8$ cycloalkenyl; optionally substituted 3- to 8-membered heterocycloalkyl; optionally substituted aryl; and optionally substituted heteroaryl;

provided that at least one of $Q_3$ and $Q_4$ is not hydrogen;

$Y_1$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —$C(O)R_{11}$; —$C(O)OR_{11}$; —$C(O)N(R_{11})(R_{12})$; —$C(O)N(R_{11})S(O)_2(R_{12})$; —$S(O)_2R_{11}$; or —$S(O)_2N(R_{11})(R_{12})$;

$Y_2$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —$C(O)R_{11}$; —$C(O)OR_{11}$; —$C(O)N(R_{11})(R_{12})$; —$C(O)N(R_{11})S(O)_2(R_{12})$; —$S(O)_2R_{11}$; —$S(O)_2N(R_{11})(R_{12})$, or —O—$Si(R_{11})_3$;

$Y_3$ is —$C(O)R_{11}$, —$COOR_{11}$, —$C(O)NHSO_2R_{11}$, —$C(O)NHSO_2NR_{11}R_{12}$, or 1,2,4-oxadiazol-3-yl-5(4H)-one, or $Y_3$ is optionally substituted aryl, optionally substituted heteroaryl, optionally substituted —$C_5$-$C_6$ cycloalkyl, or optionally substituted 5- to 6-membered heterocycloalkyl;

$Y_4$ is hydrogen, halo, optionally substituted $C_1$-$C_6$ alkyl, optionally substituted —$C_3$-$C_6$ cycloalkyl, optionally substituted 3- to 6-membered heterocycloalkyl, —CN, —$C(O)R_{11}$; —$C(O)OR_{11}$; —$C(O)N(R_{11})(R_{12})$;

—C(O)N(R$_{11}$)S(O)$_2$(R$_{12}$); —OR$_{11}$, —NR$_{11}$R$_{12}$; —SR$_{11}$; —S(O)$_2$R$_{11}$; or —S(O)$_2$N(R$_{11}$)(R$_{12}$);

alternatively, Y$_2$ and Y$_3$ are taken together to form an optionally substituted 5-12 membered heterocyclic ring or carbocyclic ring containing 1, 2, or 3 double bonds;

Z$_1$ is CR$_1$, Z$_2$ is CR$_2$, and Z$_3$ is N;

R$_1$ and R$_2$ are each independently selected from:
1) hydrogen;
2) halogen;
3) —NO$_2$;
4) Cyano;
5) Optionally substituted —C$_1$-C$_8$ alkyl;
6) optionally substituted —C$_2$-C$_8$ alkenyl;
7) optionally substituted —C$_2$-C$_8$ alkynyl;
8) optionally substituted —C$_3$-C$_8$ cycloalkyl;
9) optionally substituted 3- to 12-membered heterocycloalkyl;
10) optionally substituted aryl;
11) optionally substituted arylalkyl;
12) optionally substituted heteroaryl;
13) optionally substituted heteroarylalkyl;
14) —SR$_{11}$;
15) —S(O)$_2$R$_{11}$;
16) —S(O)$_2$N(R$_{11}$)(R$_{12}$);
17) —C(O)R$_{11}$;
18) —C(O)OR$_{11}$;
19) —C(O)N(R$_{11}$)(R$_{12}$);
20) —C(O)N(R$_{11}$)S(O)$_2$(R$_{12}$);
21) —N(R$_{11}$)(R$_{12}$);
22) —N(R$_{13}$)C(O)N(R$_{11}$)(R$_{12}$);
23) —N(R$_{11}$)C(O)(R$_{12}$);
24) —N(R$_{11}$)C(O)$_2$(R$_{12}$);
25) —N(R$_{13}$)S(O)$_2$N(R$_{11}$)(R$_{12}$);
26) —N(R$_{11}$)S(O)$_2$(R$_{12}$);
27) —OR$_{11}$;
28) —OC(O)R$_{11}$;
29) —OC(O)OR$_{11}$; and
30) —OC(O)N(R$_{11}$)(R$_{12}$); and R$_{11}$, R$_{12}$, and R$_{13}$ are each independently selected from hydrogen, optionally substituted —C$_1$-C$_8$ alkyl, optionally substituted —C$_2$-C$_8$ alkenyl, optionally substituted —C$_3$-C$_8$ cycloalkyl, optionally substituted 3- to 8-membered heterocycloalkyl, optionally substituted aryl, and optionally substituted heteroaryl; alternatively, R$_{11}$ and R$_{12}$ are taken together with the nitrogen atom to which they attached to form an optionally substituted 3-8 membered heterocyclic containing 0, 1, 2, or 3 double bonds.

2. The compound of claim 1, wherein R$_1$ and R$_2$ are each independently selected from one of the following by removal of a hydrogen atom:

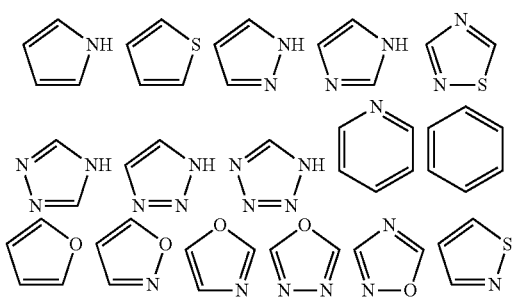

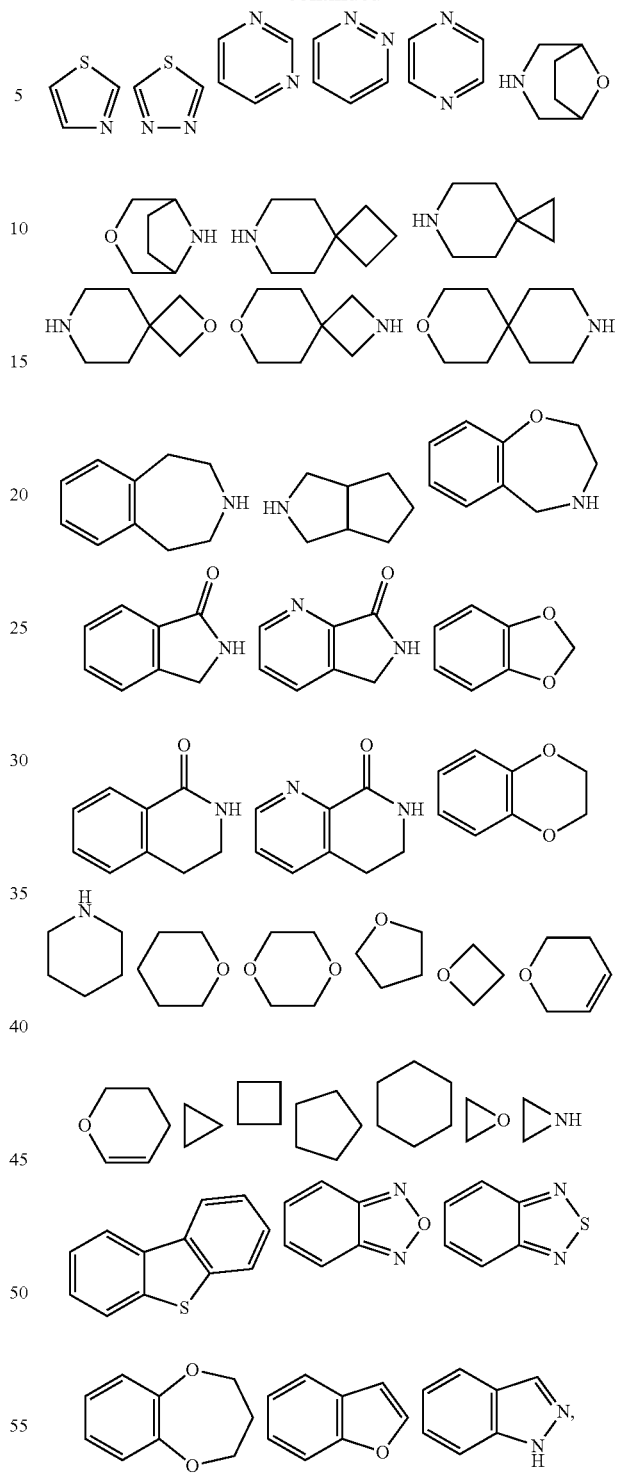

wherein each of these groups is optionally substituted with one or two groups selected from halo, CN, —OR$_{11}$, —NR$_{11}$R$_{12}$, optionally substituted C$_1$-C$_6$ alkyl, and optionally substituted 3- to 8-membered heterocyclic; and R$_{11}$ and R$_{12}$ are as defined in claim 1.

3. The compound of claim 1, represented by Formula (IV-1) or Formula (IV-2), or a pharmaceutically acceptable salt, N-oxide, or ester thereof:

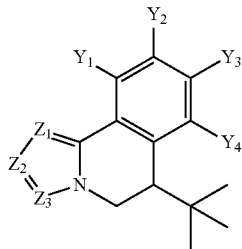
(IV-1)

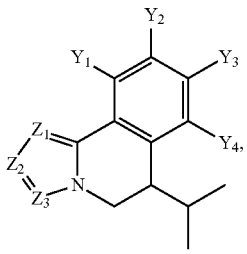
(IV-2)

wherein $Y_1$, $Y_2$, $Y_3$, $Y_4$, $Z_1$, $Z_2$, and $Z_3$ are as defined in claim 1.

4. A compound of claim 1, represented by Formula (IX-3) or Formula (IX-6), or a pharmaceutically acceptable salt, N-oxide, or ester thereof:

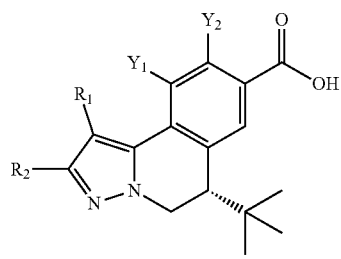
(IX-3)

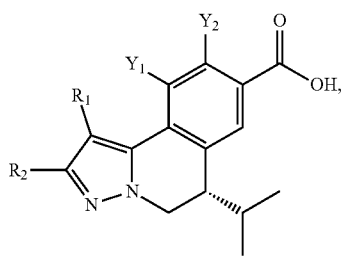
(IX-6)

wherein $Y_1$, $Y_2$, $R_1$, and $R_2$ are as defined in claim 1.

5. The compound of claim 1, represented by one of Formulae (XVIII-4) to (XVIII-6), or a pharmaceutically acceptable salt, N-oxide, or ester thereof:

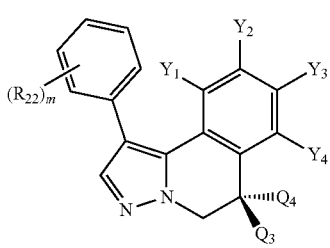
(XVIII-4)

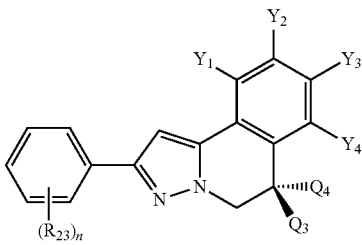
(XVIII-5)

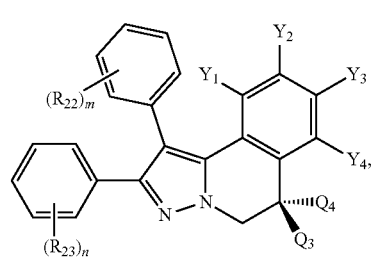
(XVIII-6)

wherein $R_{22}$ and $R_{23}$ are each independently selected from halo, CN, —$OR_{11}$, —$NR_{11}R_{12}$, and optionally substituted $C_1$-$C_6$ alkyl; m is 0, 1, 2, 3 or 4; n is 0, 1, 2, 3, or 4; and $R_{11}$, $R_{12}$, $Y_1$, $Y_2$, $Y_3$, $Y_4$, $Q_3$, and $Q_4$ are as defined in claim 1.

6. The compound of claim 1, represented by one of Formulae (XX-4) to (XX-6), or a pharmaceutically acceptable salt, N-oxide, or ester thereof:

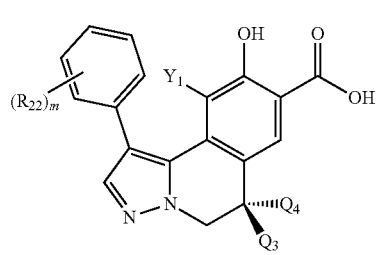
(XX-4)

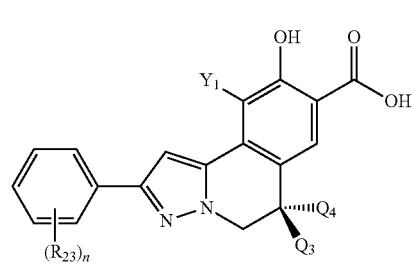
(XX-5)

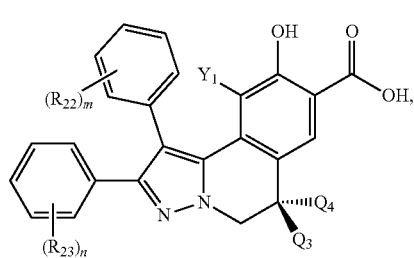
(XX-6)

wherein $R_{22}$ and $R_{23}$ are each independently selected from halo, CN, —$OR_{11}$, —$NR_{11}R_{12}$, and optionally substituted $C_1$-$C_6$ alkyl; m is 0, 1, 2, 3 or 4; n is 0, 1, 2, 3, or 4; and $R_{11}$, $R_{12}$, $Y_1$, $Q_3$, and $Q_4$ are as defined in claim 1.

7. The compound of claim 1, selected from the compounds set forth below or a pharmaceutically acceptable salt, N-oxide, or ester thereof:
| Compound | Structure | Compound | Structure |
|---|---|---|---|
| 1 | 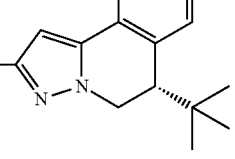 | 2 | 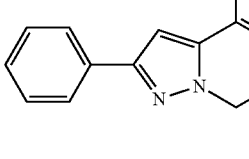 |
| 3 | 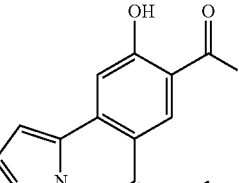 | 4 | 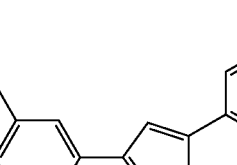 |
| 5 | 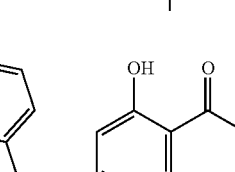 | 6 | 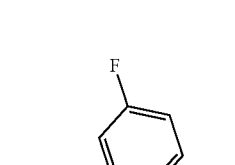 |
| 7 | 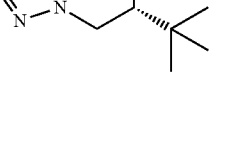 | 8 | 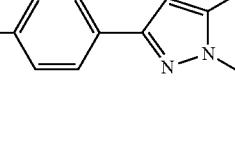 |
| 9 | 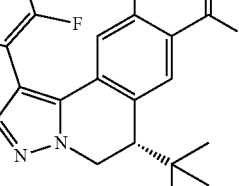 | | |

8. A pharmaceutical composition, comprising a compound according to claim 1, in combination with a pharmaceutically acceptable carrier or excipient.

9. A method of treating an HBV infection in a subject in need thereof, comprising administering to the subject a therapeutically effective amount of a compound or a combination of compounds according to claim 1.

\* \* \* \* \*